US006814756B1

(12) United States Patent
Michelson

(10) Patent No.: US 6,814,756 B1
(45) Date of Patent: Nov. 9, 2004

(54) EXPANDABLE THREADED ARCUATE INTERBODY SPINAL FUSION IMPLANT WITH LORDOTIC CONFIGURATION DURING INSERTION

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 0 days.

(21) Appl. No.: 09/574,858

(22) Filed: May 19, 2000

Related U.S. Application Data

(60) Provisional application No. 60/180,404, filed on Feb. 4, 2000.

(51) Int. Cl.[7] .................................................. A61F 2/44
(52) U.S. Cl. .................................. 623/17.11; 623/17.16
(58) Field of Search ............................ 623/17.16, 17.11

(56) References Cited

U.S. PATENT DOCUMENTS

| | | |
|---|---|---|
| 3,875,595 A | 4/1975 | Froning |
| 4,309,777 A | 1/1982 | Patil |
| 4,349,921 A | 9/1982 | Kuntz |
| 4,401,112 A | 8/1983 | Rezaian |
| 4,501,269 A | 2/1985 | Bagby |
| 4,553,273 A | 11/1985 | Wu |
| 4,554,914 A | 11/1985 | Kapp et al. |
| 4,636,217 A | 1/1987 | Ogilvie et al. |
| 4,657,550 A | 4/1987 | Daher |
| 4,714,469 A | 12/1987 | Kenna |
| 4,759,769 A | 7/1988 | Hedman et al. |
| 4,863,476 A | 9/1989 | Shepperd |
| 4,932,975 A | 6/1990 | Main et al. |
| 4,961,740 A | 10/1990 | Ray et al. |
| 5,015,247 A | 5/1991 | Michelson |
| 5,026,373 A | 6/1991 | Ray et al. |
| 5,055,104 A | 10/1991 | Ray |
| 5,059,193 A | 10/1991 | Kuslich |
| 5,062,850 A | 11/1991 | MacMillan et al. |
| 5,123,926 A | 6/1992 | Pisharodi |

(List continued on next page.)

FOREIGN PATENT DOCUMENTS

| | | |
|---|---|---|
| CA | 2151481 | 3/1995 |
| DE | 44 16 605 C1 | 6/1995 |
| SU | 1424826 A1 | 9/1988 |
| WO | WO 97/00054 | 12/1997 |
| WO | WO 98/48739 | 11/1998 |
| WO | WO 99/42062 | 8/1999 |
| WO | WO 00/12033 | 3/2000 |
| WO | WO 00/35389 | 6/2000 |
| WO | WO 00/74605 | 12/2000 |
| WO | WO 00/78253 | 12/2000 |

*Primary Examiner*—Corrine McDermott
*Assistant Examiner*—Thomas Barrett
(74) *Attorney, Agent, or Firm*—Martin & Ferraro, LLP

(57) ABSTRACT

An at least in part frusto-conical threaded interbody spinal fusion implant having an expandable height.

233 Claims, 12 Drawing Sheets

U.S. PATENT DOCUMENTS

| | | |
|---|---|---|
| 5,147,402 A | 9/1992 | Bohler et al. |
| 5,171,278 A | 12/1992 | Pisharodi |
| 5,192,327 A | 3/1993 | Brantigan |
| 5,236,460 A | 8/1993 | Barber |
| 5,258,031 A | 11/1993 | Salib et al. |
| 5,263,953 A | 11/1993 | Bagby |
| 5,290,312 A | 3/1994 | Kojimoto et al. |
| 5,306,310 A | 4/1994 | Siebels |
| 5,314,477 A | 5/1994 | Marnay |
| 5,336,223 A | 8/1994 | Rogers |
| 5,397,364 A | 3/1995 | Kozak et al. |
| 5,439,684 A | 8/1995 | Prewett et al. |
| 5,455,231 A | 10/1995 | Constantz et al. |
| 5,464,439 A | 11/1995 | Gendler |
| 5,507,813 A | 4/1996 | Dowd et al. |
| 5,507,816 A | 4/1996 | Bullivant |
| 5,522,899 A | 6/1996 | Michelson |
| 5,549,679 A | 8/1996 | Kuslich |
| 5,554,191 A | 9/1996 | Lahille et al. |
| 5,593,409 A | 1/1997 | Michelson |
| 5,609,635 A | 3/1997 | Michelson |
| 5,653,763 A | 8/1997 | Errico et al. |
| 5,665,122 A | 9/1997 | Kambin |
| 5,693,100 A | 12/1997 | Pisharodi |
| 5,702,391 A | 12/1997 | Lin |
| 5,702,455 A | 12/1997 | Saggar |
| 5,713,904 A | 2/1998 | Errico et al. |
| 5,749,916 A | 5/1998 | Richelsoph |
| 5,776,199 A | 7/1998 | Michelson |
| 5,782,832 A | 7/1998 | Larsen et al. |
| 5,800,550 A | 9/1998 | Sertich |
| 5,865,848 A | 2/1999 | Baker |
| 5,885,982 A | 3/1999 | Dolynchuk et al. |
| 5,928,284 A | 7/1999 | Mehdizadeh |
| 5,976,187 A | 11/1999 | Richelsoph |
| 5,980,522 A | 11/1999 | Koros et al. |
| 5,989,290 A | 11/1999 | Biedermann et al. |
| 6,015,436 A | 1/2000 | Schonhoffer |
| 6,019,792 A | 2/2000 | Cauthen |
| 6,039,761 A | 3/2000 | Li et al. |
| 6,045,579 A | 4/2000 | Hochshuler et al. |
| 6,080,193 A | 6/2000 | Hochshuler et al. |
| 6,087,555 A | 7/2000 | Dunstan et al. |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,129,763 A | 10/2000 | Chauvin et al. |
| 6,176,822 B1 | 1/2001 | Biedermann et al. |
| 6,183,517 B1 | 2/2001 | Suddaby |
| 6,190,414 B1 | 2/2001 | Young et al. |
| 6,190,880 B1 | 2/2001 | Israel et al. |
| 6,193,757 B1 | 2/2001 | Foley et al. |
| 6,201,039 B1 | 3/2001 | Brown et al. |
| 6,375,683 B1 | 4/2002 | Crozet et al. |
| 6,419,705 B1 | 7/2002 | Erickson |
| 6,436,140 B1 | 8/2002 | Liu |
| 6,491,724 B1 | 12/2002 | Ferree |

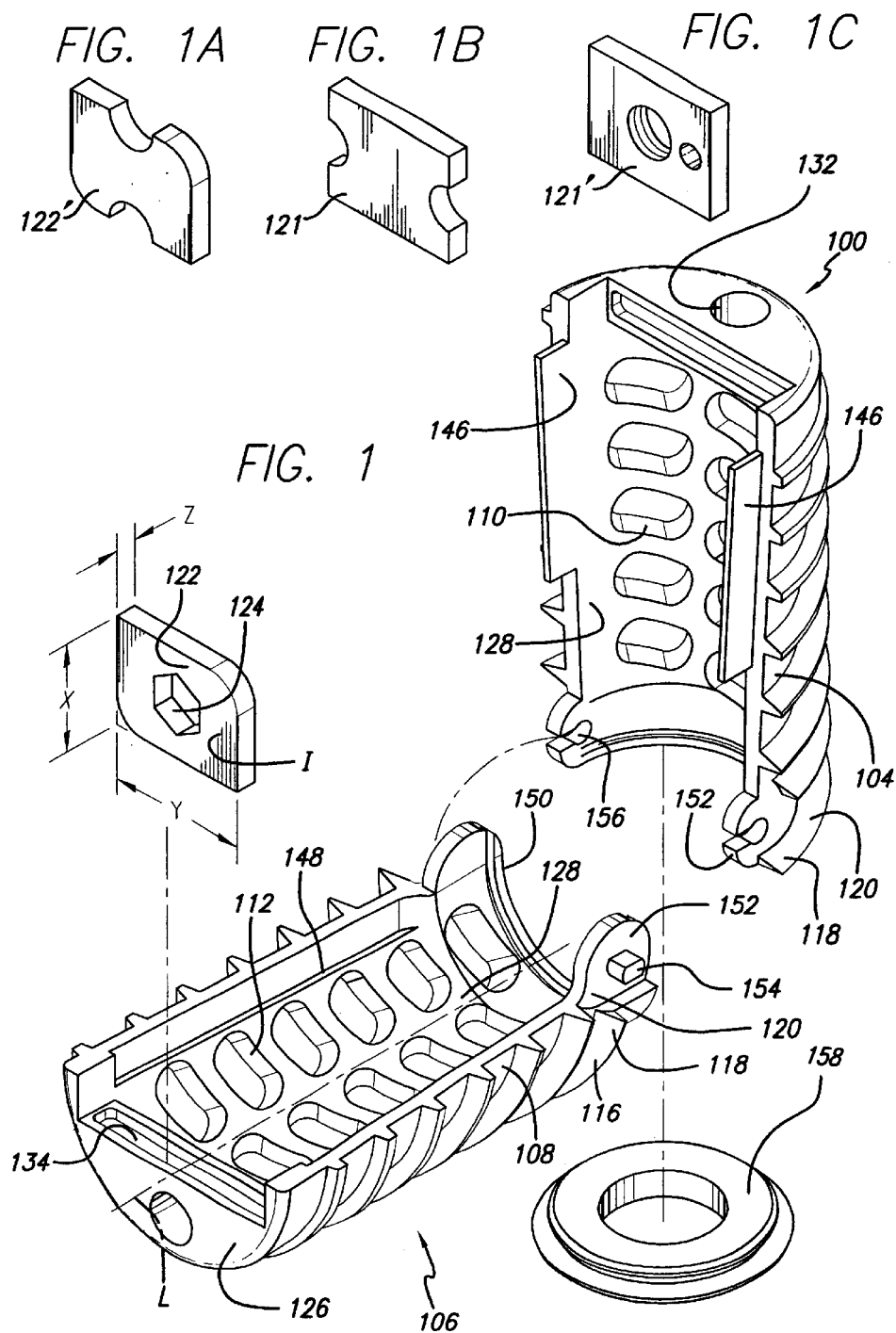

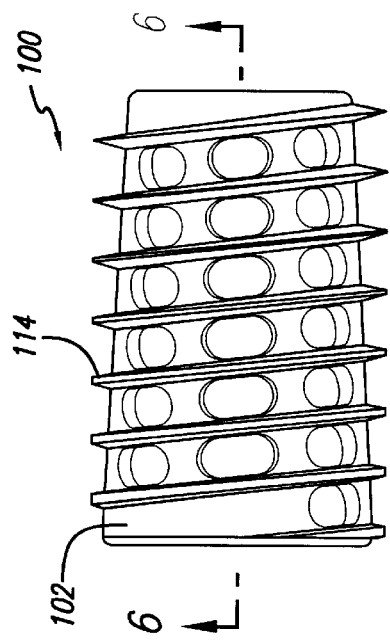
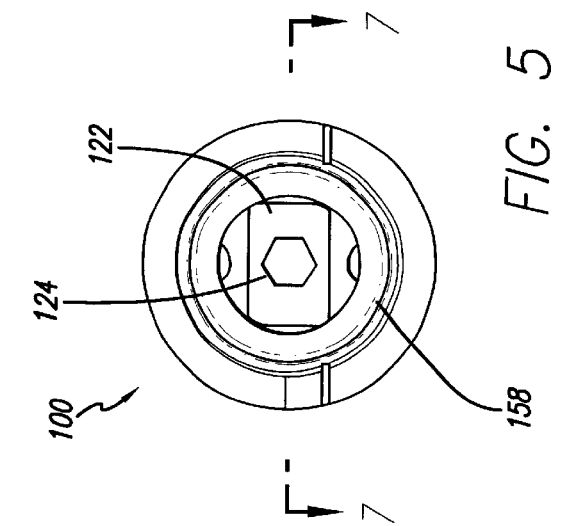
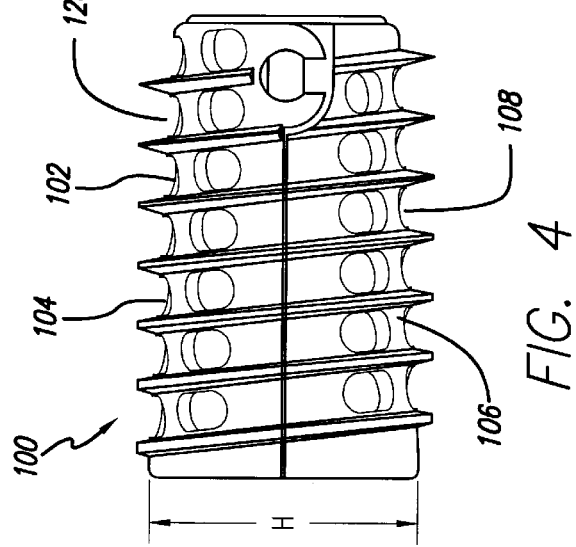
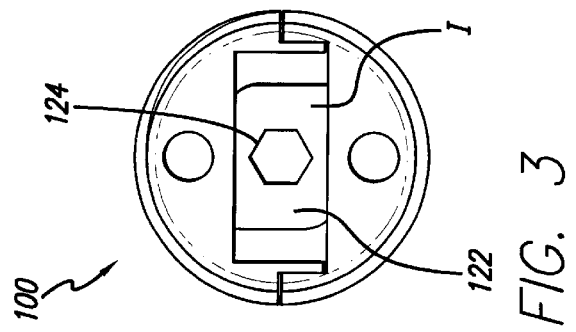

FIG. 12C
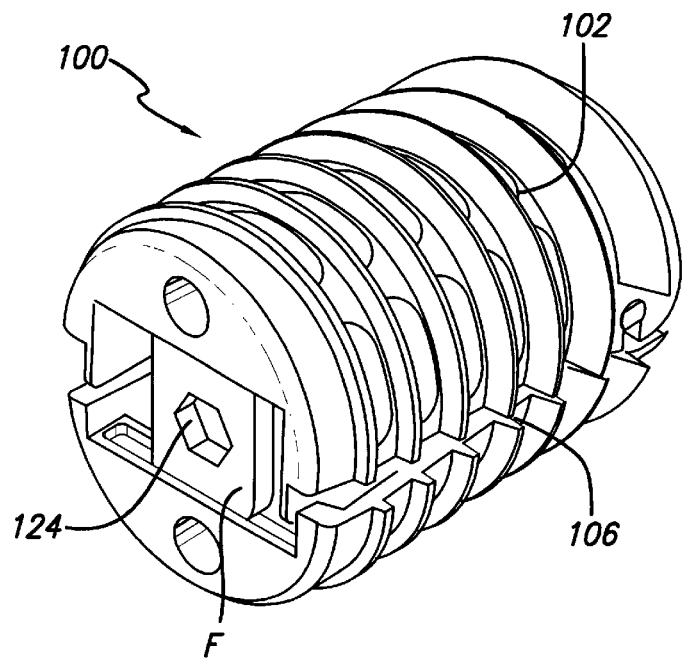
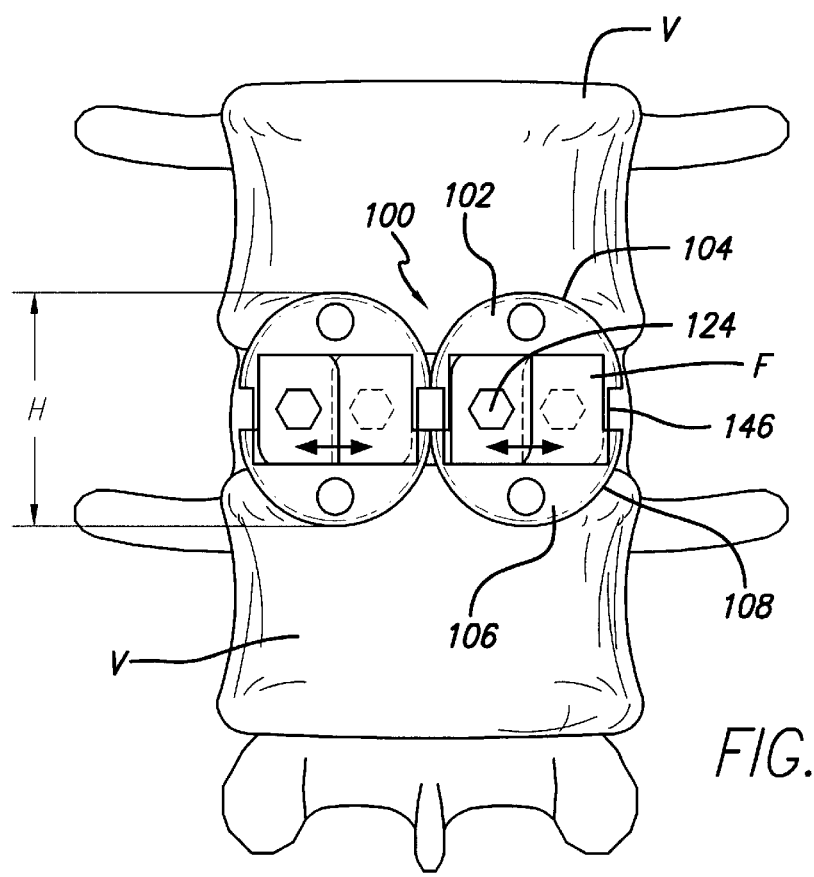
FIG. 13

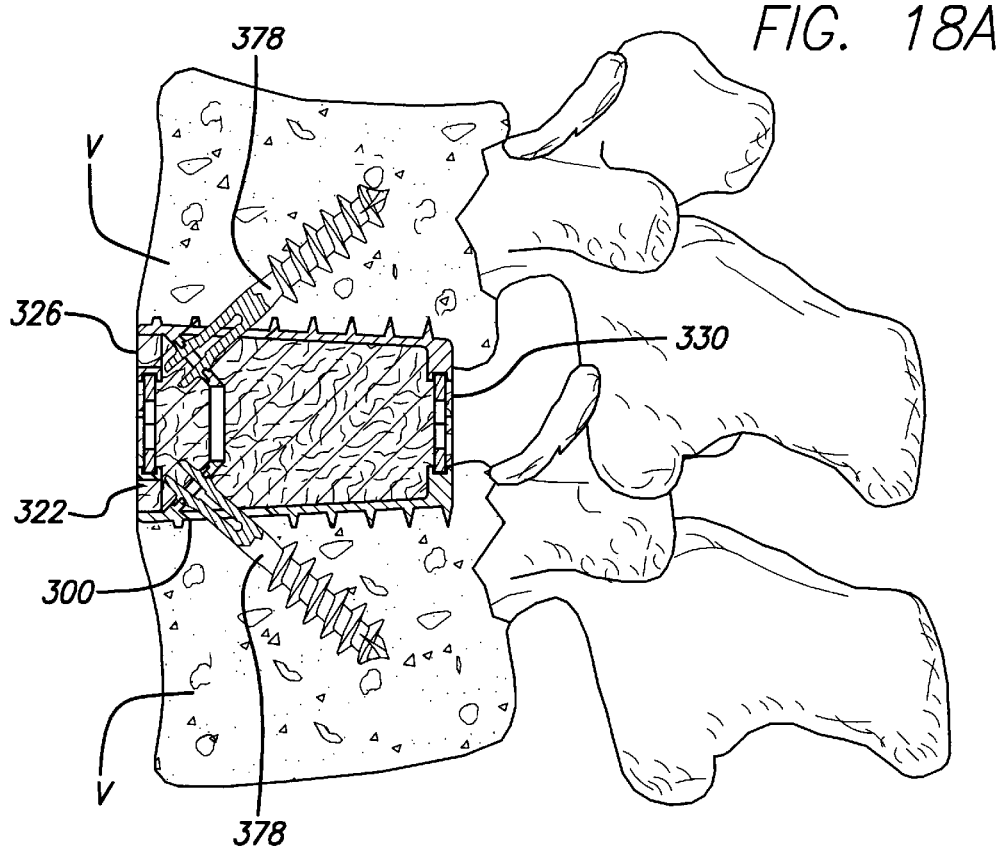
FIG. 18A
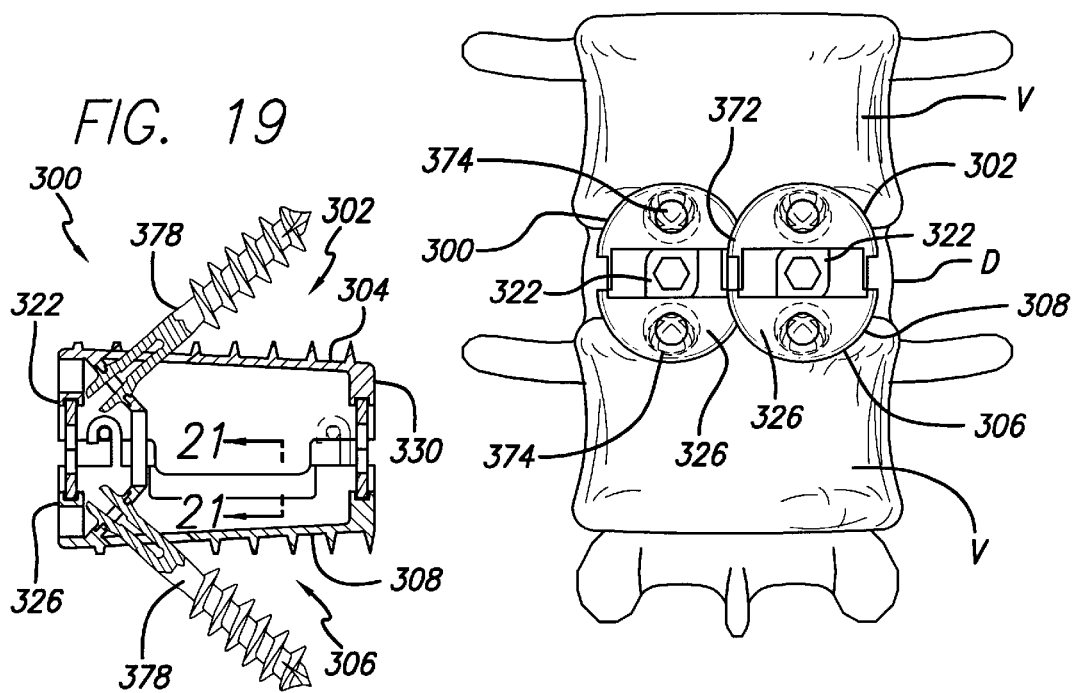
FIG. 19
FIG. 18B

EXPANDABLE THREADED ARCUATE INTERBODY SPINAL FUSION IMPLANT WITH LORDOTIC CONFIGURATION DURING INSERTION

This application claims priority to provisional application No. 60/180,404, filed Feb. 4, 2000, which is incorporated by reference herein.

BACKGROUND OF THE INVENTION

1. Field of the Invention

The present invention relates generally to an improved interbody (for placement at least in part between adjacent vertebral bodies) threaded spinal fusion implant for the immobilization of vertebrae. The present invention is directed to threaded implants only and not to non-threaded implants. In particular, the invention relates to a threaded spinal fusion implant that is selectively directionally expandable and which specifically has height raising capabilities that are utilized once the implant is initially positioned. More particularly, the invention relates to a threaded implant having arcuate portions of upper and lower members that in a first, collapsed, or insertion position are angled to one another and form at least a portion of a frusto-conical shape along a substantial portion of the length of the implant.

2. Description of the Related Art

Threaded spinal fusion implants are known in the related art. The first artificial threaded spinal fusion implant was invented by Michelson and is disclosed in U.S. Pat. No. 5,015,247, which is hereby incorporated by reference.

Lordotic, frusto-conical, or tapered, threaded spinal fusion implants are also known in the art. By way of example, Michelson has invented such implants as disclosed in U.S. application Ser. No. 08/480,904, which is hereby incorporated by reference.

Expandable fusion implants are known in the related art. The first expandable spinal fusion (allowing for the growth of bone from vertebral body to vertebral body through the implant) implant was invented by Michelson and is disclosed in U.S. Pat. No. 5,776,199, which is hereby incorporated by reference.

Lordotic, frusto-conical, or tapered, spinal fusion implants have the advantage of restoring or enhancing spinal lordosis. Threaded spinal fusion implants offer the advantage of being easily positioned in the implantation space and of having excellent fastening or holding features. Expandable fusion implants offer the advantage of allowing for the placement of a potentially larger implant through a smaller opening in a patient's body. Selective expansion along a single direction, (e.g. vertical only when correctly installed) offers the advantage of increasing the height of the implant and therefore the distraction of the disc space, but without a concomitant increase in the width of the implant.

There exists a need for an artificial interbody spinal fusion implant providing for all of the aforementioned advantages in combination.

SUMMARY OF THE INVENTION

In accordance with the present invention, as embodied and broadly described herein, there is provided an expandable threaded artificial interbody spinal fusion implant, having a shape that is generally frusto-conical when inserted, for insertion across a disc space between two adjacent vertebral bodies of a human spine. The threaded implant of the present invention includes an upper member having an arcuate portion adapted for placement toward and at least in part within one of the adjacent vertebral bodies and a lower member having an arcuate portion adapted for placement toward and at least in part within the other of the adjacent vertebral bodies. The arcuate portions of the upper and lower members have at least one opening in communication with one another for permitting for the growth of bone from a vertebral body to an adjacent vertebral body through the implant. The upper and lower members are articulated therebetween, preferably proximate one of the proximal ends and the distal ends of the upper and lower members and preferably allow for divergence between the articulating members at the end opposite the articulating end of the implant. The upper and lower members have a first position relative to one another that allows for a collapsed implant height and a second position relative to one another that allows for an increased height. The arcuate portions of the upper and lower members in the first position of the present invention are angled to one another and form at least a portion of a frusto-conical shape along the length of the implant. A portion of at least one helical thread is on the exterior of each of the opposed arcuate portions of the upper and lower members for engaging the adjacent vertebral bodies. The upper and lower members have a leading or distal end, an opposite trailing or proximal end, and a length therebetween. A blocker that is preferably in the form of an expander is located proximate at least one of the ends for holding at least a portion of the upper and lower members apart so as to maintain the increased height of the implant and resist the collapse of the implant to the collapsed implant height. Expansion of the implant preferably increases the implant height only, that is in a plane passing through the mid-longitudinal axis of the implant and the upper and lower members.

The blocker need not be in contact with the upper and lower members when the implant is initially inserted into the implantation space. The blocker may be a block or any type of spacer that is inserted between or otherwise holds apart the articulated upper and lower members after the implant is positioned so as to hold portions of the upper and lower members spaced apart the optimal height and angulation relative to one another. That is, the implant may be expanded with an extrinsic tool and then the expanded portions held apart in the second position by a third body blocker or blockers placed therebetween. Further, a physician may be able to select from a series of blockers having different heights usable with the same implant. The present invention includes expanding the implant with a tool, such as a spreader or a distractor, but is not limited to a scissors type, a rack and gear type, a threaded member type or any other type of particular external expander tool mechanism. Each tool nevertheless preferably engages the upper and the lower implant members to urge the implant apart. Then the blocker may be inserted into contact with the upper and lower members to maintain the implant at an expanded height. The height of the gap created by expanding the implant may be measured so that the appropriately sized blocker or expander may be inserted into contact with the upper and lower members depending upon the amount of distraction of the implant desired by the physician.

In a preferred embodiment, the blocker is in contact with the upper and lower members prior to the implant expansion, and the blocker is itself the expander, which may be operated by an extrinsic tool. By way of example only, the expander may rotate: to increase the height of the implant; in a single direction; more than 40 degrees and less than 140 degrees and more preferably approximately 90 degrees to move from a first insertion position to a second/deployed position; and in a plane perpendicular to the longitudinal axis of the implant to increase the height of the implant. The expander preferably remains in the same perpendicular plane relative to the longitudinal axis of the implant when rotated. In another embodiment the expander may be a member, such as a plate, a rod, or of any other configuration suitable for the intended purpose initially within the interior between the upper and lower members in a collapsed position that is erected to a more erect position when the implant is in the expanded position. The expander can be hollow or solid.

In a preferred embodiment, the expander preferably has means including, but not limited to, an opening, a projection, or a detent adapted to cooperatively engage a tool used to rotate the expander to increase the height of the implant. The opening, projection, or detent is adapted to cooperatively engage a tool that preferably rotates about an axis parallel to the longitudinal axis the implant to rotate the expander to increase the height of the implant. Rather then having an opening, a projection, a detent, or a central aperture, the expander may have two or more recesses or holes placed on or through the proximal face to engage a tool. In an alternative embodiment of the expander, cutouts may be positioned along a portion of the perimeter of the expander.

The expander is preferably located proximate at least one of the proximal end or the distal end of the upper and lower members. The expander, however, need not be so located. The expander may be spaced away from the end and even permit a hollow portion to exist on both the proximate and distal sides of the expander. The upper and lower members preferably have an interior surface therebetween and a hollow defined therein with the expander located proximate one of the longitudinal ends of that interior hollow. The hollow between the ends of the upper and lower members is preferably unobstructed by the expander so as to permit growth of bone directly through the hollow unobstructed by the expander from vertebral body to vertebral body through the implant transverse to the longitudinal axis of the implant. The implant may comprise a second and lesser hollow extending at least in part from the expander to the end of the upper and lower members proximate that expander. A preferred expander mechanism includes an expander in combination with cooperating surfaces of the end wall of the implant that guide and support the expander.

Preferred forms of interbody spinal fusion implants have a substantial hollow portion. Certain expandable interbody spinal fusion implants that increase in height only of the related art contain an expansion mechanism passing longitudinally therethrough or an expansion mechanism that is configured for movement of the expansion mechanism from proximate one end of the hollow portion to proximate the other end of the hollow portion, thus requiring the expander to pass through the length of the hollow portion. A preferred embodiment of the present invention overcomes these limitations.

The expander moves the arcuate portions of the upper and lower members from an angled orientation to a parallel orientation relative to one another; from a first angled orientation to a second angled orientation relative to one another; or from a first height at each end to a second and greater height at at least one and possibly both ends, but in each event the arcuate portions of the upper and lower members in the first or insertion position are angled to one another over a substantial portion of the length of the implant, and/or form at least a portion of a frusto-conical shape along the length of the implant. Each of the upper and lower members may structurally cooperate with a blocker, or expander so as to keep it located so as to function for its intended purpose. By way of example, each of the upper and lower members preferably has a track within which the blocker may be captured or the expander rotated. The tracks may be configured to permit the expander to rotate therein and then to move from side to side therewithin. The track of the upper member and the track of the lower member are preferably in the same plane and the plane is preferably perpendicular to the longitudinal axis of the implant.

A preferred expander has a first height in a first or insertion position and a greater second height when rotated or positioned into a second or deployed position to increase the maximum height of the implant from a first maximum height to a second maximum height. By way of example, at least one of the tracks of the upper and lower members preferably has a cooperating surface and the expander has a corresponding cooperating surface that contacts the cooperating surface of the track to orient the expander in a predetermined position. The cooperating surfaces preferably orient the expander within the implant such that the axis of rotation of the expander is parallel with the longitudinal axis of the implant and, more preferably, center the expander within the implant such that the axis of rotation of the expander coincides with the longitudinal axis of the implant. As may be advantageous for the further loading of the implant with fusion-promoting material, the expander may cooperate with the tracking surfaces of the upper and lower members to allow the expander to slide from side-to-side for easier access to the implant interior.

The implant is preferably packed full of bone or other fusion-promoting substances prior to expansion of the implant. Expansion of the implant results in a space being formed in the implant interior into which additional fusion promoting substances such as bone may preferably be packed. Rotating the expander within the implant causes a void that can be filled with bone. If the expander is configured to permit side-to-side movement, then packing of additional bone into the implant is easy.

When installing a preferred implant from the posterior approach to the spine, the implant is driven from the trailing end and the expander is at the leading end at the anterior aspect of the spine. When expanded, the implant installed from the posterior aspect leaves a void at the leading end of the implant near the anterior aspect of the spine because the leading end of the implant has been made taller, the void is preferably packed with bone. Additionally, the path left behind in the bone filled interior of the implant by the tool used to access the expander through the bone filled interior to position the expander is preferably packed with bone as well.

In a preferred embodiment of the present invention, the expander height change from the first position to the second position corresponds to substantially the same change in height of the implant along at least a portion of the length of the implant. The expander may be configured in different ways. A preferred configuration for a rotational expander includes: a first dimension corresponding to the width of the expander when the implant is initially inserted into the spine and to the height of the rotational expander when the rotational expander is rotated to increase the height of the implant; and a second dimension corresponding to the height of the expander when the implant is initially inserted into the spine and to the width of the expander when the expander is rotated to increase the height of the implant. The first dimension preferably is greater than the second dimension.

The expander may have an upper surface, a lower surface, and side surfaces as defined when the expander is positioned after rotation to increase the height of the implant. As used herein, the term "side surfaces" refers to those portions of the expander that extend from the upper member to the lower member after the expander has been rotated into its second or deployed position to increase the height of the implant. The "upper" and "lower" expander surfaces refer to those portions of the expander that are in contact with the upper and lower members when the implant is in its second or expanded configuration. Each of the upper and lower surfaces of the expander may lie generally in a plane and may be generally parallel to one another. The side surfaces and the upper and lower surfaces may be oriented so as to substantially form a parallelogram, which will typically be in the shape of a rectangle generally.

A preferred expander is in the form of a modified rectangle or rhomboid. The expander generally has a longer dimension and a shorter dimension. When the expander is in a first position, the short dimension spans the distance between the upper and lower members and when the expander is in the second position, the expander's long dimension spans the distance between the upper and lower members.

The expander may have a cross-section with the side surfaces intersecting the upper and the lower surfaces at junctions, which may be two diametrically opposed corners and two diametrically opposed arcs. The two diametrically opposed arcs may be each of the same radius and, preferably, the diagonal or modified hypotenuse "MH" between the opposed arcs has a maximum dimension that generally approximates the distance between the upper and lower surfaces such that, when the expander is rotated from a first insertion position toward a second/deployed position, no substantial over-distraction occurs between the adjacent vertebral bodies as would occur if the height of the implant was increased markedly beyond that obtained in the second/deployed position. The two diametrically opposed corners may form a 90-degree angle. The expander preferably has a fixed shape during movement from a first insertion position to a second/deployed position within the implant.

In a preferred embodiment, a modified hypotenuse or diagonal "MH" is the dimension between the two diametrically opposed arcs that allows for the rotation of the expander from a first position to a second position without substantial over-distraction occurring during this process. The phrase "without substantial over-distraction" is defined as distracting the vertebral bodies in the range of elastic deformation and short of plastic deformation and tissue failure. To avoid any ambiguity regarding the phrase "without over-distraction," this phrase and the individual words contained therein are not being used as they may be in their normal or ordinary use, but are being used as defined in this application only. In the example of this rotational expander, the MH could be identical in length to the height thereby assuring literally no overdistraction. It may be preferred, however, to have the MH just slightly greater in length than the height to insure the stability of the expander in the expanded or second position because this would then require additional force over the stable position to derotate the expander.

In accordance with an embodiment of the present invention, a second expander may be located between the upper and lower members for moving at least a portion of the upper and lower members away from one another to increase the height of the implant as defined by the maximum distance between the arcuate portions of the upper and lower members proximate that expander. All of the features described herein for the expander may also be applicable to the second expander. Additionally, the second expander may be located proximate an end of the implant opposite the other expander, thereby providing an implant capable of being expanded at both ends of the implant. The increased height of the implant resulting from moving the two expanders may be constant or varied along the length of the implant according to the desired configuration of the implant and the relative dimensions of the individual expanders. A given implant may be adapted to receive or cooperatively engage a series of progressively sized (taller) blockers or expanders to allow the surgeon to make a final height selection at the time of surgery.

In accordance with an embodiment of the present invention, the implant may include an expansion mechanism including the expander and at least one partial wall structure preferably located proximate an implant end that guides and holds the expander in a predetermined position.

The implant may have an overlapping step-cut wall junction between the upper and lower members, which offers as some of its advantages: increasing the lateral rigidity of the implant, holding the implant in the closed first position until expanded, and to the extent desired retaining the fusion-promoting materials within the implant. The wall junction may be either solid or perforated.

One of the upper and lower members preferably has an interior wall extending toward the other of the upper and lower members and, more preferably, has two interior walls extending from each side of the arcuate portion. The interior walls may be aligned parallel with the longitudinal axis of the implant. The other one of the upper and lower members preferably has an interior-contacting surface adapted to contact or receive the interior longitudinal wall.

By way of example, one of the upper and lower members may have a longitudinally extending interior wall, which is preferably unexposed, extending toward the other of the upper and lower members when the implant is in an initial insertion position. When the implant is in the final expanded or deployed position the implant has a preferred shape such that each of the arcuate portions of the upper and lower members are separated by at least a portion of interior wall, which in this position preferably has an exposed side.

The upper and lower members in certain embodiments are articulated to one another so one of the respective ends of the upper and lower members remain articulated while the other of the respective ends of the upper and lower members are free to move away from one another. In a preferred embodiment, the articulating means is achieved without a third member, such as an axle shaft, for example, passing through the implant. The articulating means preferably is formed into the implant walls themselves, and in a further preference in such a way that the two-implant halves may be articulated when at 90 degrees to each other. The halves then are moved, much like a book closing, toward each other prior to insertion into the implantation space in the spine. Once the upper and lower members are closed from the approximately 90 degrees articulating position, much like closing the leaves of a book, the upper and lower members of the implant are locked together at the articulation so that the members will not disarticulate when in use. Other types of articulation as would be known to one of ordinary skill in the art are within the scope of the present invention.

By way of example, the upper and lower members preferably have a cooperating rotational articulation or pivot point between a proximate one of the proximal end and the distal end of the upper and lower members. The cooperating rotational articulation preferably is proximate one of the proximal end and the distal end of the upper and lower members at an end opposite the expander when only one end is to be expanded. A preferred rotational articulation configuration includes cooperating brackets and projections configured such that articulation therebetween occurs when the upper and lower members are substantially perpendicular to one another. Such a configuration offers the advantage that the brackets and the projections will not disengage one another when articulated for use such as insertion into the spine and subsequent expansion within a range of movement of the upper and lower members resulting from the expander positioning.

When the implant is in the final or expanded position the implant may take the general form of a frusto-conical shape split along a horizontal plane through its mid-longitudinal axis wedged upper half from lower half by an inclined plane.

At least one and preferably both of the upper and lower members may have a screw hole passing through the trailing end, which preferably is adapted to receive a screw passing through the end of the upper and lower members and from the interior of the implant into each of the adjacent vertebral bodies to anchor the implant, further stabilize those vertebral bodies relative to each other, prevent undesirable motion at the vertebral body implant interfaces, increase the compressive load at the implant trailing end, prevent rocking and thereby to mitigate against excessive peak loads, and to more uniformly distribute loads imparted to the implant over the length of the implant to the adjacent vertebral bodies. The implant may have a side configured, when in the expanded position, to cooperate with another interbody spinal fusion implant so as to allow the pair of implants to have a reduced combined width.

The trailing end of the implant preferably has a tool-engaging portion, but the implant may be adapted to cooperatively engage a driver at another location or by any means as would be known to one of ordinary skill in the art. This tool-engaging portion is adapted to engage an insertion tool that holds and rotates the implant into position. The configuration of the tool-engaging portion may be an opening, and more particularly an opening that is along the longitudinal axis of the implant to facilitate the use of an insertion tool that rotates the implant into an inserted position. It is appreciated that the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting the implant. In specific embodiments, the leading or trailing end may have wall portions, and/or be adapted to cooperatively engage a cap. Either the end wall portions or a cap may have an opening or openings, which may function to hold fusion-promoting materials within the implant and/or, permit vascular access and bone growth therethrough.

For an embodiment of an implant of the present invention having one expander, the main access opening is preferably at the end opposite from the expander. The main opening may be at either the distal or proximal end of the implant. The end of the upper and lower members containing the expander may serve as a secondary access opening.

By way of example, an implant configured for insertion from an anterior approach may be initially packed from the distal or leading end of the implant. The implant is then driven into position. Once the expander is moved into final position and any associated tool for positioning the expander is withdrawn from the expander, any void in the bone packed into the implant interior may be filled. The expander may be moved from side-to-side to pack more bone into the implant. In essence, the side-to-side movement of the expander provides for a secondary access opening for accessing the hollow interior of the implant and for compressively loading it with fusion-promoting substances. The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

BRIEF DESCRIPTION OF THE DRAWINGS

FIG. 1 is an exploded perspective view of a spinal fusion implant of one embodiment of the present invention;

FIG. 1A is a perspective view of an alternative embodiment of a blocker in the form of an expander for use with the spinal fusion implant of FIG. 1;

FIG. 1B is a perspective view of another alternative embodiment of a blocker for use with the spinal fusion implant of FIG. 1;

FIG. 1C is a perspective view of yet another alternative embodiment of a blocker for use with the spinal fusion implant of FIG. 1;

FIG. 2 is a top plan view of the implant of FIG. 1;

FIG. 3 is a trailing end view of the implant of FIG. 1;

FIG. 4 is a side elevation view of the implant of FIG. 1;

FIG. 5 is a leading end view of the implant with the end cap there attached of FIG. 1;

FIG. 12C is a trailing end perspective view of the implant of FIG. 1 with the implant in an expanded position;

FIG. 13 is a trailing end view of the anterior aspect of two adjacent vertebral bodies and two implants of FIG. 1 implanted therebetween in a final position;

FIG. 18A is a cross-sectional side view of the implantation site formed across the space between two adjacent vertebral bodies and one of the implants of FIG. 17 installed into the implantation space;

FIG. 18B is a trailing end view of the anterior aspect of two adjacent vertebral bodies and the implant of FIG. 17 implanted therebetween in an expanded position as well as another embodiment designed to be used as a side-by-side pair;

FIG. 19 is a cross-sectional side view of the implant of FIG. 18A without bone or other fusion-promoting substances shown therein for the purpose of illustrating a preferred configuration for articulating the upper and lower members together with a hook and peg configuration that prevents the implant from over expanding and with an alternative second hook and peg shown on the right hand side of the figure in dashed lines;

DESCRIPTION OF THE PREFERRED EMBODIMENTS

Figure 6:
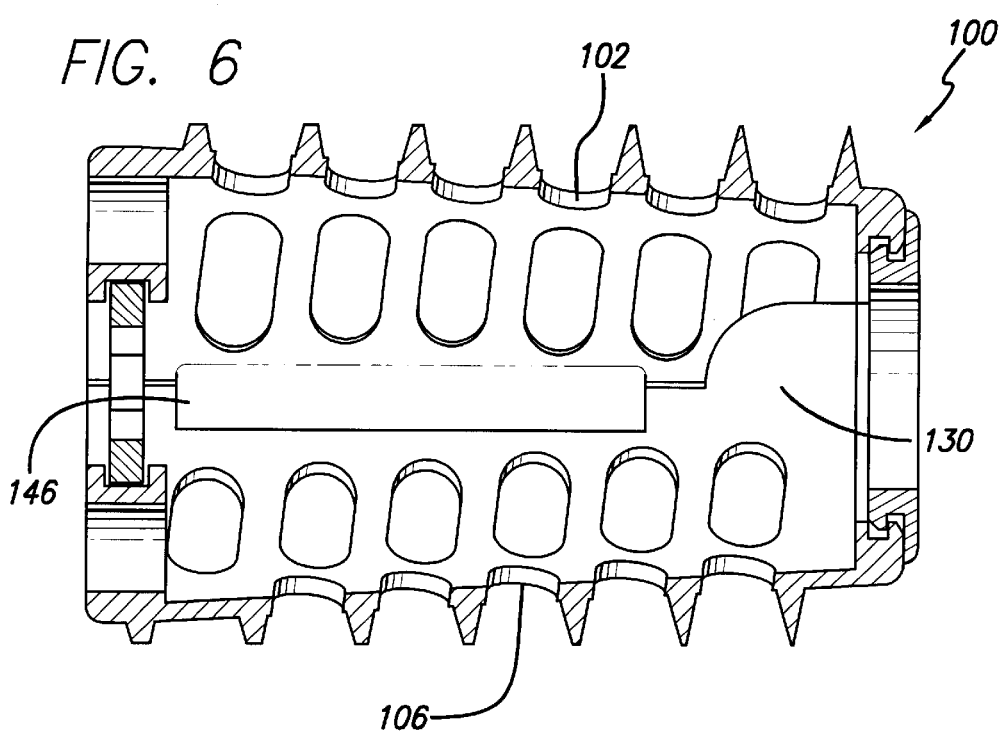
FIG. 6 is a cross-sectional view along line 6—6 of FIG. 2.
Figure 7:
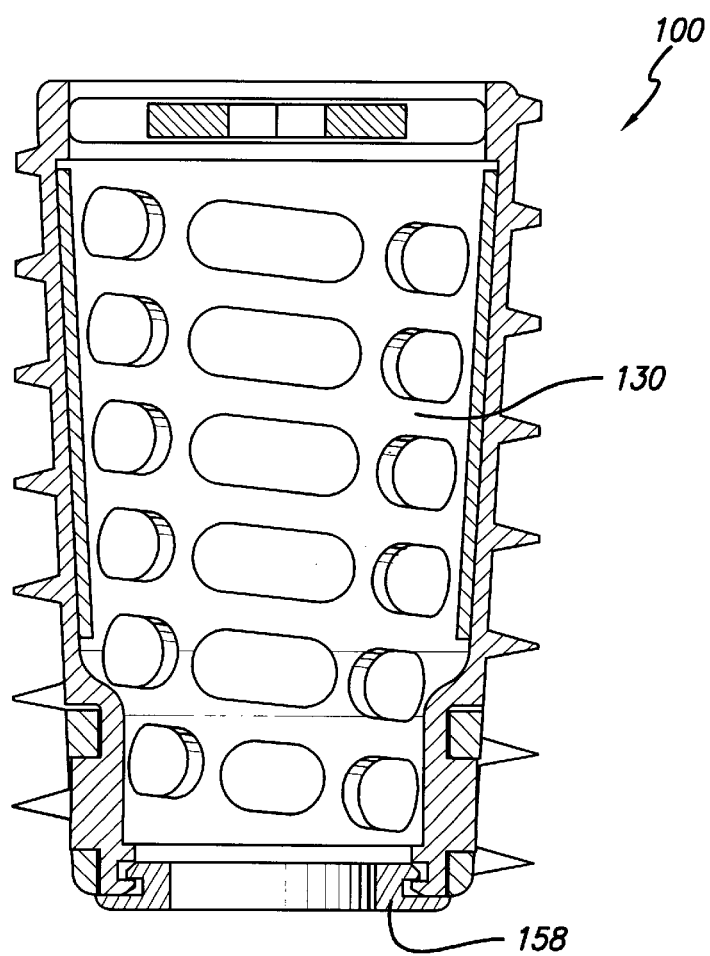
FIG. 7 is a cross-sectional view along line 7—7 of FIG. 5.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings.

Shown in FIGS. 1–7 and 10–13, in accordance with the present invention, as embodied and broadly described herein, is one embodiment of an expandable threaded artificial interbody spinal fusion implant 100 for anterior insertion across a disc space D between two adjacent vertebral bodies V of a human spine. Threaded implant 100 of the present invention includes an upper member 102 having an arcuate portion 104 adapted for placement toward and at least in part within the upper of the adjacent vertebral bodies V and a lower member 106 having an arcuate portion 108 adapted for placement toward and at least in part within the lower of the adjacent vertebral bodies V. Arcuate portions 104, 108 of upper and lower members 102, 106 have at least one opening 110, 112 in communication with one another for permitting for the growth of bone from vertebral body V to adjacent vertebral body V through implant 100. Upper and lower members 102, 106 are articulated therebetween at an adjacent one of the proximal ends and the distal ends of upper and lower members 102, 106 and allow for rotation between the articulating members at the end opposite the articulating end of implant 100. Upper and lower members 102, 106 have a first position relative to one another that allows for a collapsed implant height and a second position relative to one another that allows for an increased height. Arcuate portions 104, 108 of upper and lower members 102, 106 in the first position of the present invention are angled to one another and form at least a portion of a frusto-conical shape along the length of implant 100. A portion 114, 116 of at least one thread 118 is on an exterior 120 of each of opposed arcuate portions 104, 108 of upper and lower members 102, 106 for engaging adjacent vertebral bodies V.

While a specialized form of a blocker 121 is described in significant detail below with reference to expander 122, blocker 121 need not be in contact with upper and lower members 102,106 when implant 100 is initially inserted into the implantation space. Blocker 121 may be a block or any type of spacer that is inserted between the articulated upper and lower members 102, 106 after implant 100 is positioned so as to hold portions of the upper and lower members 102, 106 spaced apart the optimal height and angulation relative to one another. That is, the implant may be expanded with an extrinsic tool and then the expanded portions held apart in the second position by a third body blocker placed therebetween. Further, a physician may be able to select from a series of blockers having different heights usable with the same implant. The present invention includes expanding the implant with a tool, such as a spreader or a distractor but is not limited to a scissors type, a rack and gear type, a threaded member type or any other specific type of movement mechanism. Each tool nevertheless preferably engages upper and lower implant members 102, 106 to urge them apart. Blocker 121 is then inserted into contact with upper and lower members 102,106 to maintain implant 100 at an expanded height. The height of the gap created by expanding implant 100 may be measured so that the appropriately sized blocker 121 or specialized blocker, expander 122, may be inserted in implant 100 depending upon the amount of distraction of implant 100 desired by the surgeon.

Blocker 121 that is preferably in the form of expander 122 is located proximate at least one of the ends of the implant upper and lower members 102, 106 and holds at least a portion of upper and lower members 102, 106 apart so as to maintain the increased height of implant 100 and resist the collapse of implant 100 to the collapsed implant height. Expander 122 in the present embodiment increases the implant height as measured in a plane passing through the mid-longitudinal axis of implant 100 and upper and lower members 102, 106 during positioning of expander 122 and as may be desirable is capable of selectively increasing the height of the implant only.

Figure 10:
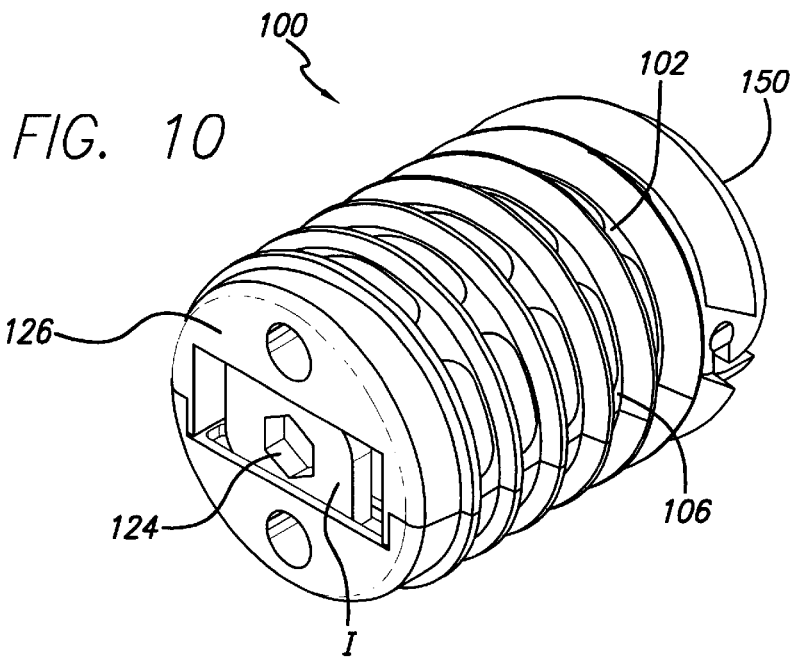
FIG. 10 is a trailing end perspective view of the implant of FIG. 1.

Expander 122 in the present embodiment is adapted to rotate in a single direction approximately 90 degrees to move from an initial (first) insertion position 1, as best shown in FIGS. 1, 3 and 10, to a final (second) deployed or expanded position F, as best shown in FIG. 13, to increase the maximum height H of implant 100. Expander 122 preferably rotates in a plane perpendicular to the longitudinal axis L of implant 100 to increase the maximum height H of implant 100. During rotation, expander 122 remains in the same perpendicular plane relative to the longitudinal axis L of the implant. It is appreciated that an expander within the scope of the present invention may be designed to: rotate in either direction or both directions; rotate more than 40 degrees and less than 140 degrees; rotate more or less than 90 degrees; or rotate in a plane other than perpendicular.

Expander 122 has an opening 124 adapted to cooperatively engage a tool (not shown) used to rotate expander 122 to increase height H of implant 100. Opening 124 is adapted to cooperatively engage a tool that preferably rotates about an axis parallel to the longitudinal axis L of implant 100 to rotate expander 122 to increase height H of implant 100. Opening 124 also may be used as a passageway to pass fusion-promoting substances through expander 122 and into implant 100. It is appreciated that the expander may also include a projection, a detent, or any other configuration in place of or in addition to an opening so as to cooperatively engage a tool to move the expander.

In an alternative embodiment, an expander 122' could have cutouts along any portion of its perimeter not involved in the actual rotation as shown in FIG. 1A. In another alternative embodiment, a blocker 121 having cutouts along a portion of its perimeter can be positioned into the implant as shown in FIG. 1B. The cutouts can be used to engage a raised area within the implant to lock blocker 121 or expander 122' into position or be used by the surgeon to grasp blocker 121 with a tool that cooperatively engages the cutouts to facilitate inserting blocker 121 into the implant. Rather then having an opening, a projection, a detent, or a central aperture, a blocker 121' alternatively could have two or more recesses or holes placed on or through the proximal face to engage a tool as shown in FIG. 1C.

Figure 14:
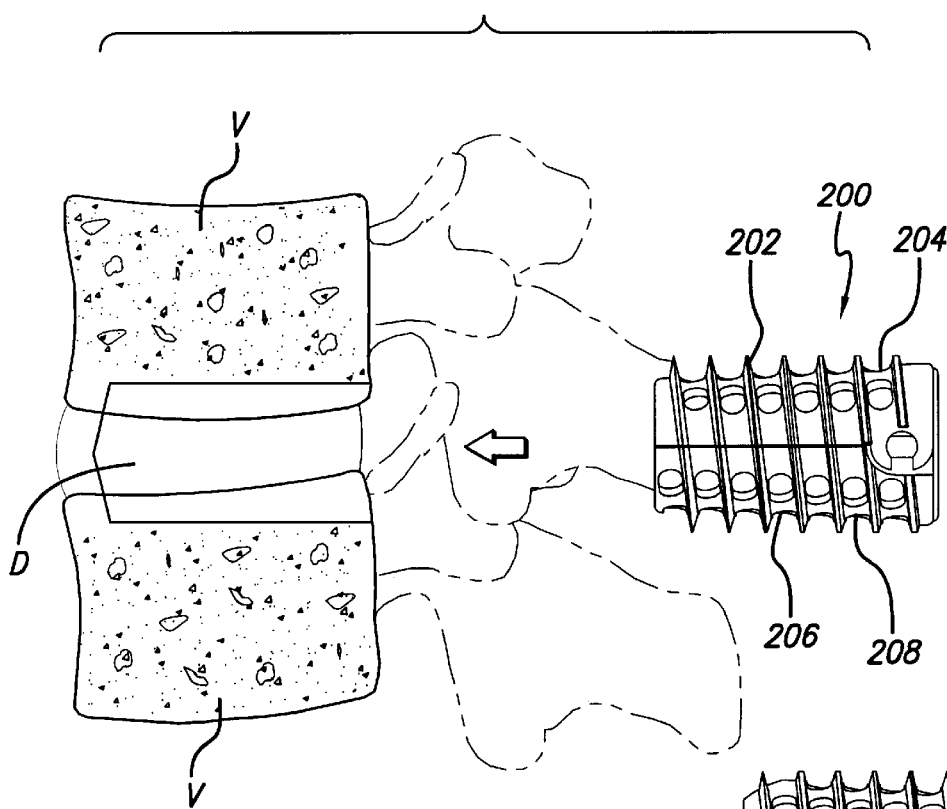
FIG. 14 is a cross-sectional side view of an implantation site formed posteriorly across the disc space between two adjacent vertebral bodies and a second embodiment of an implant of the present invention for posterior insertion being installed into the implantation site.
Figure 15:
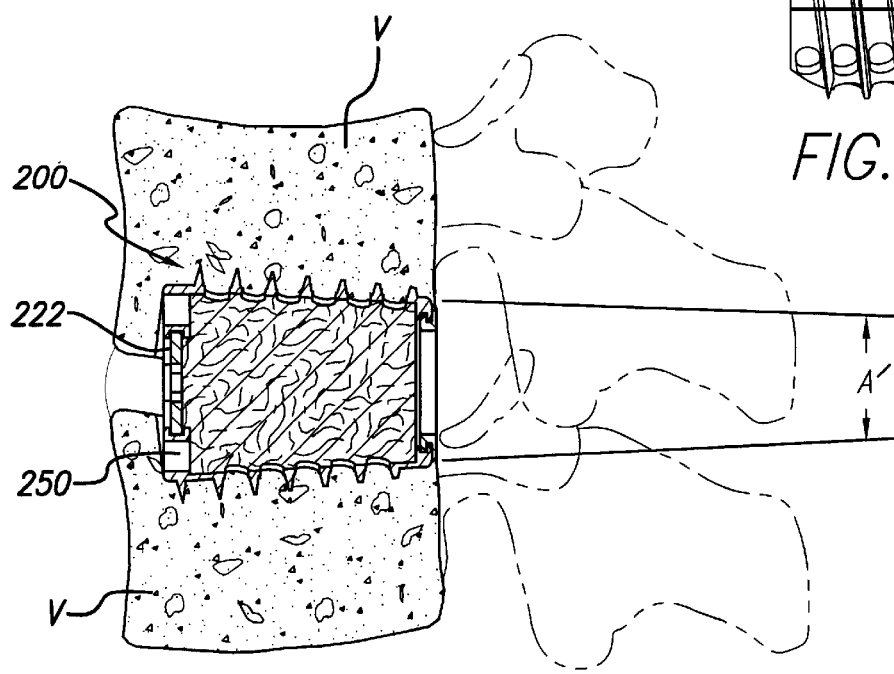
FIG. 15 is a cross-sectional side view of the implantation site formed across the space between two adjacent vertebral bodies and the implant of FIG. 14 installed into the implantation space.
Figure 16:
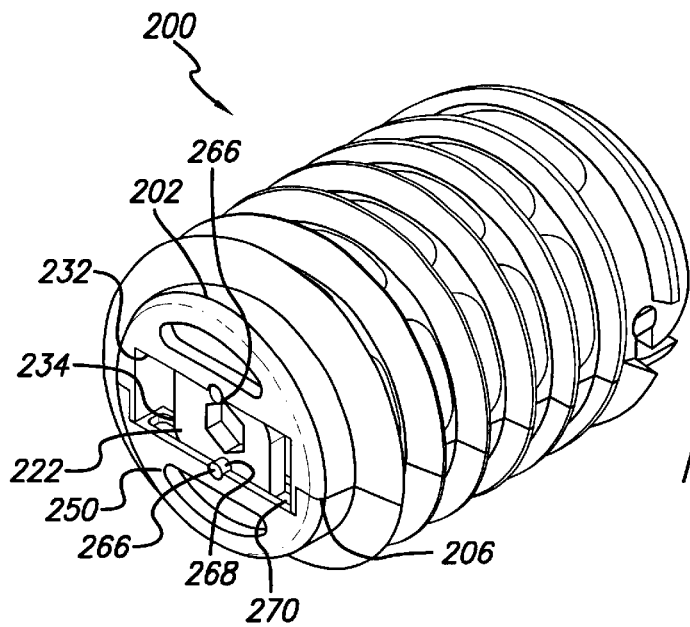
FIG. 16 is a leading end perspective view of the implant of FIG. 14.

As shown in FIGS. 1, 6, 7, 10, 12A–12C, and 13, in one preferred embodiment of the present invention for anterior insertion, expander 122 is located proximate the trailing end 126 of upper and lower members 102,106. While in a second embodiment as shown in FIGS. 14–16 for posterior insertion, expander 222 is located proximate the leading end 250. As shown if FIGS. 17–19, in third and fourth embodiments of the present invention for anterior insertion and possible use together, expanders 322 are located proximate each of leading and trailing ends 330, 326 of implants 300.

Implant 100 preferably has an interior surface 128 and a hollow 130 defined therein. Expander 122 of the present embodiment is located proximate interior surface 128 and more particularly proximate interior surface 128 at trailing end 126 of upper and lower members 102,106. As is preferred, hollow 130 between the ends is unobstructed by expander 122 so as to allow for the unimpeded loading of the interior of the implant with the desired fusion-promoting substances; thus, loading the implant is easy. Further, this preferred configuration of implant 100 makes available all of the volume of the hollow to contain fusion-promoting substances and so as to permit for the growth of bone directly through the hollow unobstructed by the expander to adjacent vertebral bodies V. Unobstructed hollow 130 further allows for packing implant 100 with fusion-promoting substances. It is appreciated that depending on the intended results, the expander also may be located at distal end 126 or leading end 150 of upper and lower members 102,106 or anywhere else within the implant. The unobstructed hollow preferably has no mechanism extending along the longitudinal axis of the implant when finally deployed and the mechanism that moves the implant from a first position to a second position preferably does not move expander 122 longitudinally through the hollow portion. The expander may work by pivoting on a surface in contact with an interior wall portion of at least one of the upper and lower members 102, 106. Moreover, multiple expanders may be used in contact with upper and lower members 102,106 at any location within the implant.

An alternative embodiment of an expander used with the present invention includes an expander having an external thread that cooperates with converging threaded portions of the upper and lower members 102, 106 to expand the implant as the expander is rotated into position. Another alternative embodiment of an expander includes an expander having a cam configuration to expand the implant upon rotation.

The mechanism or tool used to move the expander is not part of the implant itself as the mechanism or tool is removed from the implant upon moving the expander, e.g. such as to rotate it into place and thus expand the implant to the final expanded position.

Figure 11:
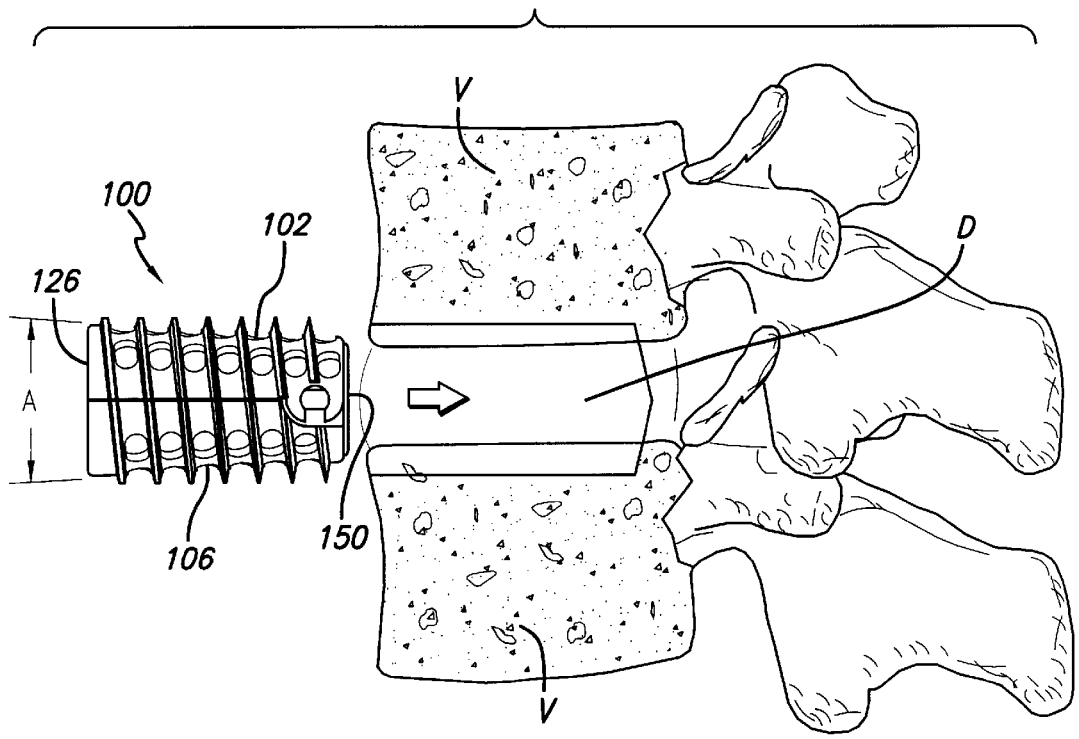
FIG. 11 is a side view of the implant of FIG. 10 being inserted from a generally anterior approach to the spine into an implantation site formed across a disc space and two adjacent vertebral bodies of the spine shown in partial cross-section.
Figure 12A:
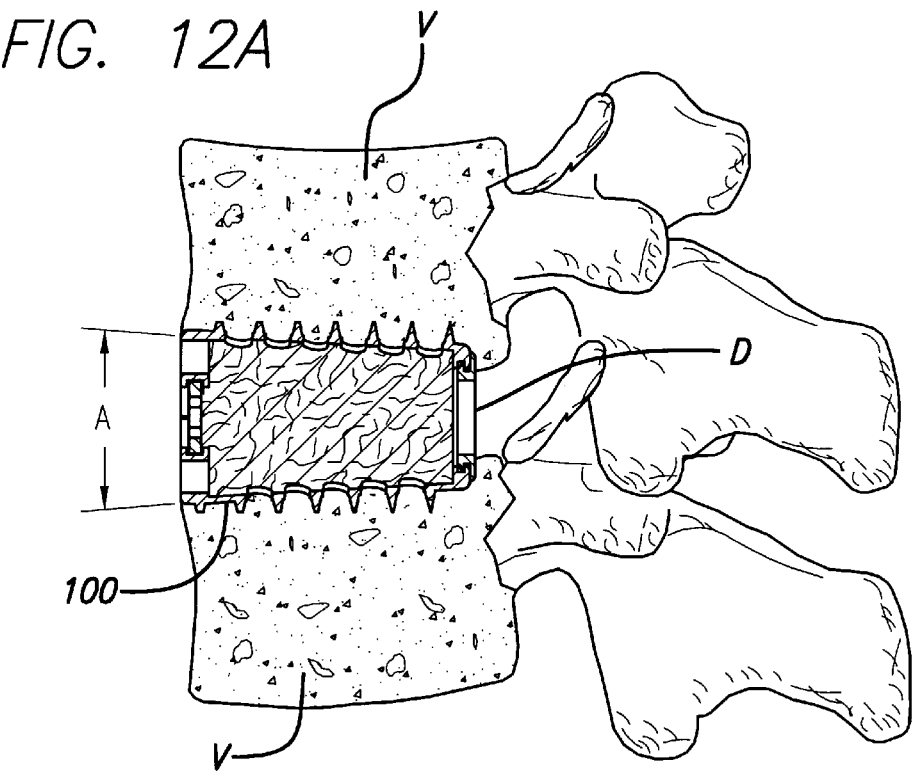
FIG. 12A is a cross-sectional view of the implant of FIG. 1 inserted in an implantation site formed across the disc space and two adjacent vertebral bodies of the spine.
Figure 12B:
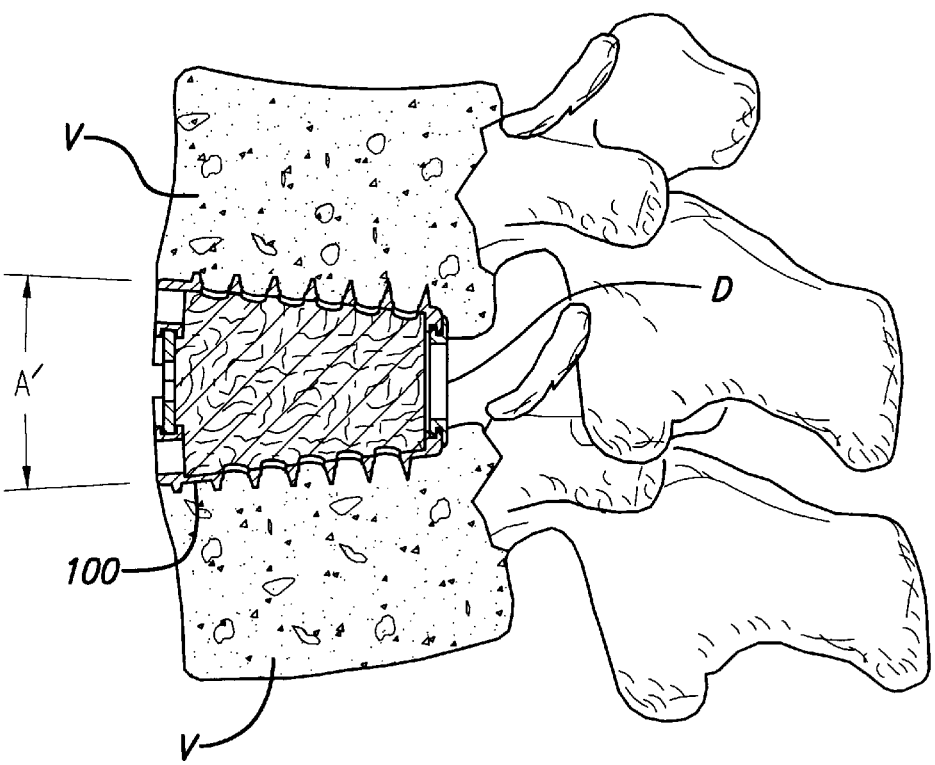
FIG. 12B is a cross-sectional view of the implant of FIG. 1 inserted in an implantation site of FIG. 12A and expanded to place the adjacent vertebral bodies in proper lordosis.

Expander 122 of the present embodiment moves arcuate portions 104, 108 of upper and lower members 102, 106 from a first angled orientation A, as shown in FIGS. 1 and 11 in a first position, to a second angled orientation A', as shown in FIG. 12B where implant 100 has a generally oblong cross section at trailing end 126, in a second position. The implant of the present invention need not be a true frusto-conical shape as a cross section need not form a complete circle but may have portions of the perimeter absent, less round, flattened including flattened on two or more sides, or other. It is appreciated that the expander also may move the arcuate portions of the upper and lower members from a first height at each end to a second and greater height at each end.

In this embodiment, each of upper and lower members 102, 106 structurally cooperate with expander 122 so as to keep it located so as to function for its intended purpose. Each of upper and lower members 102, 106 of the implant of FIG. 1 has a track 132, 134 within which expander 122 rotates. As best shown in FIGS. 1 and 13, track 132, 134 is configured to permit expander 122 to rotate therein and then to move from side to side within track 132, 134. Track 132 of upper member 102 and track 134 of lower member 106 are in the same plane and the plane is perpendicular to the longitudinal axis of implant 100. It is appreciated that the track of the upper and lower members may be in different planes. Such a track design may be used with an expander with a step in it or with offset tabs to engage tracks in different planes than one another. As with the expander, the tracks also may be at various angles to the longitudinal axis of the implant including parallel with the longitudinal axis of the implant. Other means for respectively engaging the implants and the expander position thereof are anticipated and within the scope of the present invention.

Figure 9:
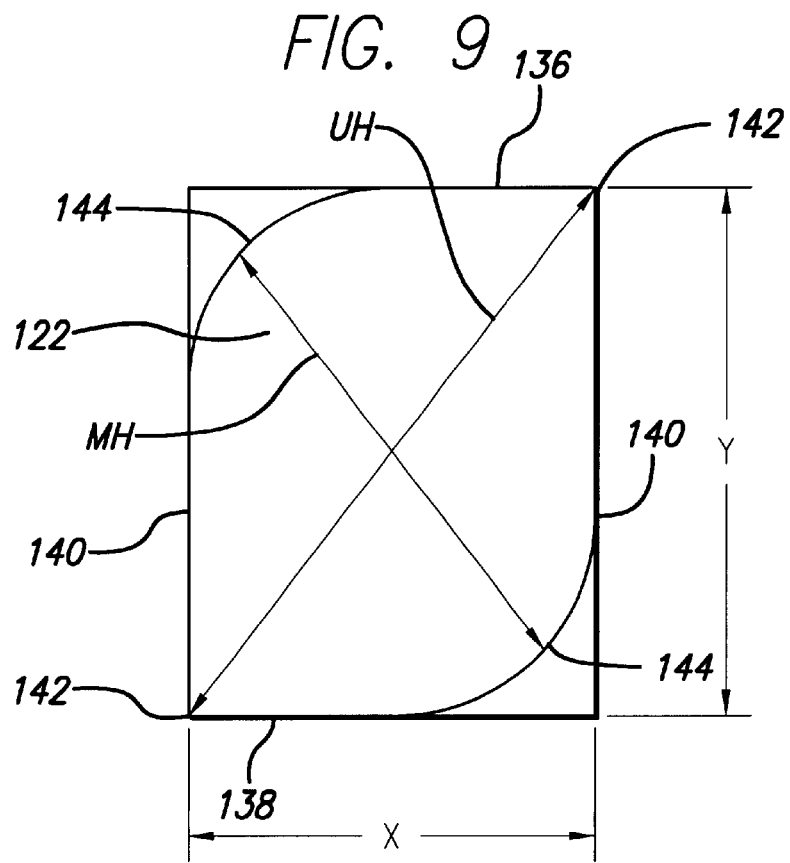
FIG. 9 is a schematic representation of a geometric configuration of a cross-section of an expander in accordance with one embodiment of the present invention.

In rotating the expander, the longer dimension of the expander is substituted for the lesser dimension of the expander thus correspondingly increasing the maximum height of the implant from the first to the second position. As best shown in FIG. 9, the schematic representation of a geometric configuration of a cross-section of an expander 122 in accordance with one embodiment of the present invention, includes: a first dimension X corresponding to the height of expander 122 when implant 100 is initially inserted into the spine and to the width of expander 122 when expander 122 is rotated to increase height H of implant 100; and a second dimension Y corresponding to the width of expander 122 when implant 100 is initially inserted into the spine and to the height of expander 122 when expander 122 is rotated to increase height H of implant 100. Second dimension Y is greater than first dimension X. Expander 122 has an upper surface 136, a lower surface 138, and side surfaces 140 as defined when expander 122 is positioned after rotation to increase height H of implant 100. As used herein, the term "side surfaces" refers to those portions of expander 122 that extend from upper member 102 to lower members 106 after expander 122 has been rotated into its final deployed, or second position to increase the height H of implant 100. The "upper" and "lower" surfaces refer to those portions of expander 122 that are in contact with upper and lower members 102, 106 when implant 100 is in its second position and configuration and is fully expanded.

A preferred expander 122 is in the form of a modified rectangle or rhomboid. The expander generally has a longer dimension Y and a shorter dimension X. When the expander is inserted into a first position, the short dimension X spans the distance between upper to the lower members 102, 106 and when expander 122 is in the second position, the longer dimension Y of expander 122 spans the distance between upper and lower members 102, 106.

Expander 122 in one embodiment of the present embodiment has a cross-section with side surfaces 140 intersecting upper and lower surfaces 136, 138 at two junctions which may be diametrically opposed corners 142 and two diametrically opposed arcs 144. Arcs 144 are preferably each of the same radius and the modified hypotenuse MH between opposed arcs 144 generally approximates the distance between upper and lower surfaces 136, 138 such that, when expander 122 is rotated from an initial insertion position toward a final deployed position, no substantial over-distraction occurs between adjacent vertebral bodies V.

The modified hypotenuse MH of this embodiment of the present invention may be equal, slightly less than, or slightly greater than dimension Y of expander 122. Having the modified hypotenuse MH be slightly greater than the dimension Y offers the advantage of having expander 122 stabilized by an over-center position, such that more energy would be required to derotate the expander than for it to remain in the deployed or second position. By "without substantial over-distraction" what is meant is that the modified hypotenuse MH length is closer to the expander dimension Y than to the unmodified hypotenuse UH; and is selected to allow the implant to preferably operate in the range of elastic deformation of the tissues about the operated disc space. Corners 142 may form, but not necessarily, a 90-degree angle and have an unmodified hypotenuse dimension UH.

By way of example, consider one embodiment of expandable implant 100 of the present invention having an optimum expanded height of 18 mm for a given implantation space. Any implant bigger than 18 mm should not be used in this implantation space because during expansion of the implant, its height would move through the range of elastic deformation of the surrounding tissues and after that, the implant would crush the vertebral bone or tear ligaments. Inserting an expander such that when the implant is fully expanded allows the implant to be 18 mm would be ideal. It may be that an implant having a 17.5 mm expanded height for this implantation space is nearly as good, but a 16 mm expanded height may be too short to fit tightly within the implantation space. Using a preferred rectangular expander without any modification to the hypotenuse that is adapted to expand the implant to the optimum 18 mm final height would require the expander to have a hypotenuse causing the implant to exceed the 18 mm expanded height temporarily during rotation of the expander. So turning the expander without a modified hypotenuse would break the vertebrae or tear the ligaments. In reverse, if one could not expand the implant to more than 18 mm without causing damage to the spine, then an implant selected to have an expander having a full unmodified hypotenuse so as to upon rotation temporarily cause the implant height to be 18 mm would in the finally expanded position allow the implant height to collapse such that there would be insufficient height for the implant to adequately distract the implantation space. Generally, the modified hypotenuse of the expander is closer in length to dimension Y of the expander than to the unmodified hypotenuse.

As best shown in FIG. 1 in this particular embodiment, expander 122 has a depth dimension Z that is less than that of first and second dimensions Y, X. Expander 122 of the present embodiment has a fixed shape during movement from initial insertion position I to final deployed position F within implant 100.

Figure 22A:
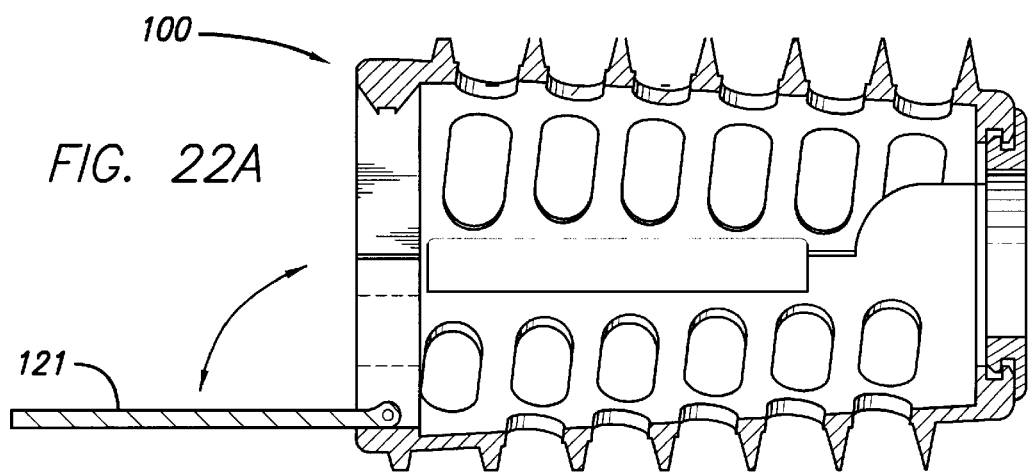
FIG. 22A is a cross-sectional side view of an alternative embodiment of an implant of the present invention with a pivoting trailing end that is also a blocker in the trailing end in the open position.
Figure 22B:
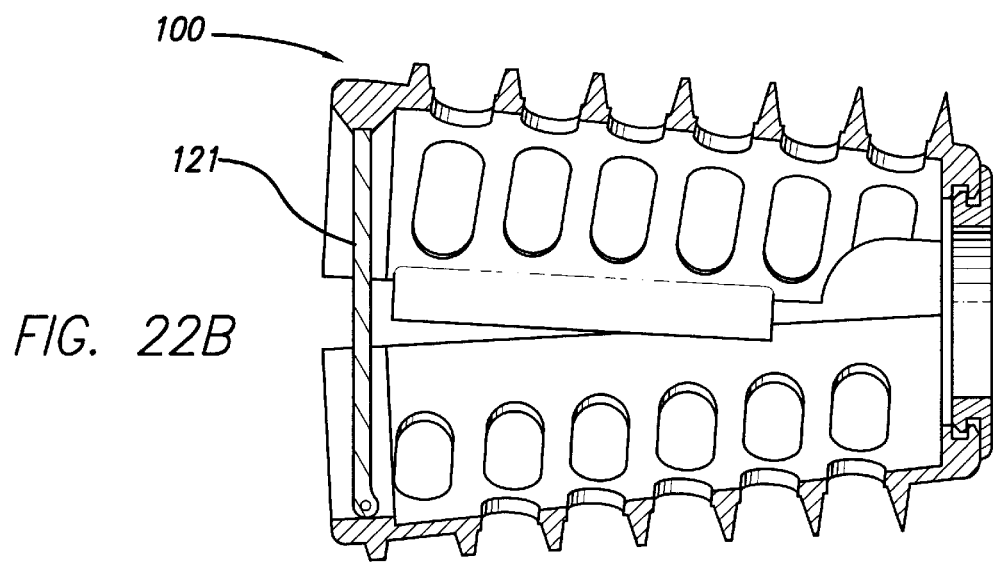
FIG. 22B is a cross-sectional side view of an alternative embodiment of an implant of the present invention with a pivoting trailing end that is also a blocker with the trailing end in the closed position.
Figure 23:
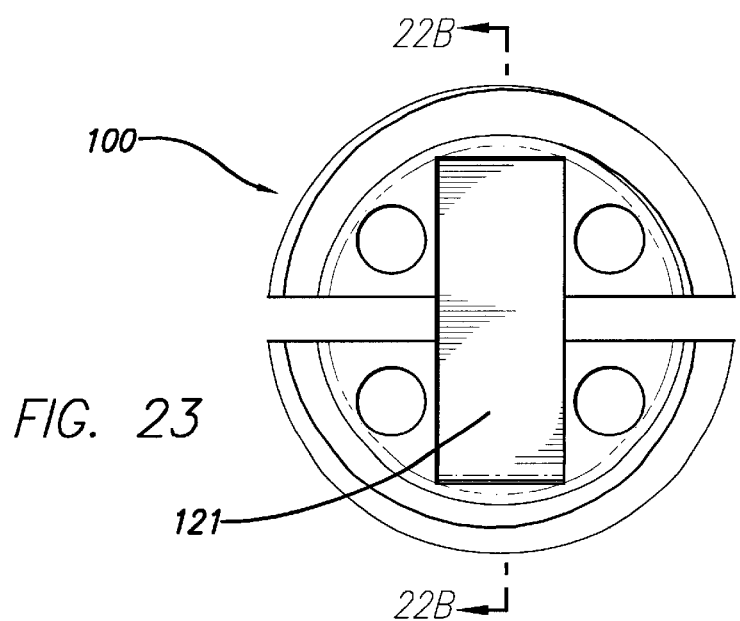
FIG. 23 is a trailing end perspective view of the implant of FIG. 22B.

As shown in FIGS. 22A, 22B, and 23, blocker 121 may also take the form of a trailing wall that articulates or hinges to the inside of implant 100. The trailing wall may be left open during insertion of implant 100 so as to trail behind the upper and lower members. The trailing wall does not protrude outside of a projection rearward of the circumference of implant 100. Once implant 100 is implanted into position, the trailing wall is rotated about one of its ends and pushed into position and locked into place. This may occur by having the trailing wall contact an inclined plane that leads up to a notch into which the trailing wall locks into place. The trailing wall itself may also have at least one opening in it to permit the further loading of fusion-promoting materials into implant 100.

While modified hypotenuse MH is illustrated as being between arcs 144 in this preferred embodiment, the configuration of expander 122 to form modified hypotenuse MH can take many forms, such that those junctions are relieved so as to have the desired lesser dimension therebetween, including arcs, chamfers, a series of angled surfaces, or any other shape so long as the modified hypotenuse MH is sufficiently reduced in dimension to function for the intended purpose according to the present teaching.

An embodiment of the present invention where modified hypotenuse MH is slightly greater than height Y offers the advantage of an over-center effect that locks expander 122 into place. In this instance, once expander 122 rotates past the diagonal of the modified hypotenuse MH, more force would be required to rotate it back from the final deployed position to its insertion position than in an embodiment where modified hypotenuse MH is equal to or less than height Y. Preferably, expander 122 offers a surgeon multiple sensory advantages including: the tactile feel of expander 122 going over center and locking into place; the visual of the handle of a tool rotating expander 122 such that the tool handle goes from perpendicular to parallel, the reverse, or other, to the disc space into place; and auditory from the sound of expander 122 snapping into place.

Each of upper and lower surfaces 136, 138 of expander 122 of the present embodiment lie generally in a plane and are generally parallel to one another. For any implant it is anticipated that a physician may be able to select from a series of blockers or expanders allowing for varying the increase in the implant height. Side surfaces 140 and upper and lower surfaces 136, 138 are oriented so as to substantially form a parallelogram. Any of a number of configurations for the expander for increasing the height of the implant is possible, based on the teachings of the present application and such configurations as would be known to one of skill in the art are anticipated within the scope of the present invention.

The implant may preferably have an overlapping step-cut wall junction between upper and power members 102, 106 which offers the advantage of increasing the lateral rigidity of implant 100 holding the implant in the closed first position until expanded, and to the extent desired retaining the fusion-promoting materials within. The wall junction may be either solid or perforated. As best shown in FIG. 1, upper member 102 in one embodiment of the preferred invention has interior walls 146 extending from each side of arcuate portion 104 toward lower member 106. Interior wall 146 is aligned parallel to longitudinal axis L of implant 100. Lower member 106 has an interior-contacting surface 148 adapted to contact or receive interior wall 146.

In a preferred embodiment, upper and lower members 102, 106 are articulated to one another so one of the respective ends of upper and lower members 102, 106 remain articulated while the other of the respective ends of upper and lower members 102, 106 are free to move away from one another. In a preferred embodiment the articulating means is achieved without a third member such as an axle shaft passing through the implant. The articulating means preferably is formed into the implant walls themselves in such a way that the two implant halves may be articulated when the halves are at 90 degrees to each other and then the halves are moved toward each other for insertion into the implantation space in the spine. The two halves are closed much like the cover of a book. The halves are locked together such that disarticulation will not occur when the implant is assembled for use. Any of a number of ways of articulating or joining upper and lower members 102, 106 is possible.

As best shown in FIG. 1 in this embodiment, upper and lower members 102, 106 of the present embodiment have a pivot point between adjacent distal ends 126 or leading ends 150 of upper and lower members 102, 106. The pivot point in the present embodiment is at the end of implant 100 opposite expander 122. The pivot point of the present embodiment operates as a hinge or axle 152 but is formed out of the walls themselves so as to preferably not intrude into the implant interior or hollow or to block access thereto. Hinge 152 includes a projection 154 extending radially from each side of arcuate portion 108 of lower member 106 and a slotted bracket 156 extending from each side of arcuate portion 104 of upper member 102 for engaging projection 154. Brackets 156 and projections 154 are configured such that engagement occurs when upper and lower members 102, 106 are substantially perpendicular to one another. Brackets 156 and projections 154 are configured so as not to disengage within a range of movement of upper and lower members 102, 106 that would occur when the implant is in use either during insertion or resulting from the expansion in height of implant 100.

As best shown in FIG. 11, interior wall 146 of upper member 102 of the present embodiment is unexposed when implant 100 is in initial insertion position I. As shown in FIG. 12C, when implant 100 is in the expanded position F, implant 100 has a shape such that each of arcuate portions 104, 108 of upper and lower members 102, 106 are separated by at least a portion of interior wall 146, which in this position has an exposed side. The exposed side of the present embodiment is smooth and flat.

Figure 8:
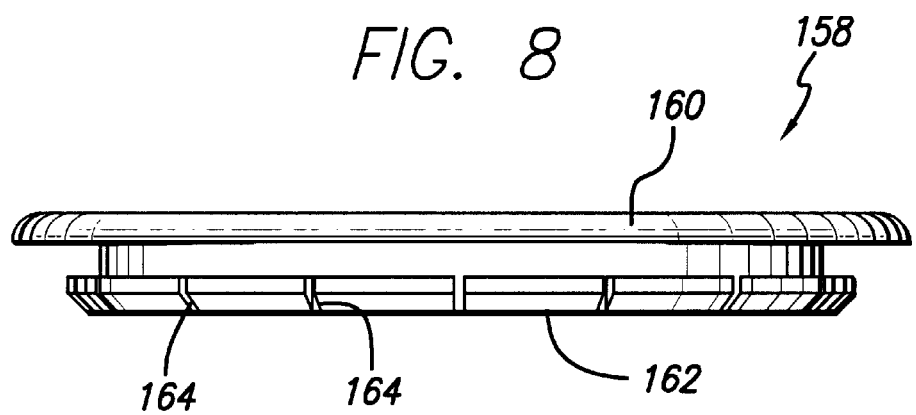
FIG. 8 is a side elevation view of an end cap for use with the implant of FIG. 1.

As best shown in FIG. 8, a cap 158 having an exterior surface 160 and an interior surface 162 is used to close leading end 150 of implant 100. Interior surface 162 of cap 158 has spaced slots 164 about its circumference to facilitate a snap fit between cap 158 and implant 100. Cap 158 and implant 100 can of course be adapted for either or both ends of implant 100.

As discussed above, implant 100 has a leading end 150 and a trailing end 126. One of the ends preferably has a tool-engaging portion. This tool-engaging portion is adapted to engage an insertion tool that holds and rotates implant 100 into position. The tool-engaging configuration may be an opening, and more particularly an opening that is along the longitudinal axis of the implant to facilitate the use of an insertion tool that rotates implant 100 into an inserted position. Of course, the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting implant 100. The opening either alone on the proximal end of implant 100 or in conjunction with other openings on the proximal end function to hold fusion-promoting material in implant 100 while permitting vascular access and bone growth through the opening or openings.

Implants of the present invention may have an end adapted to cooperatively engage an implant driver. The anterior approach implant may have a leading end, trailing end, or both ends that are adapted to engage a cap. One of the purposes for that cap includes restricting the passage of fusion-promoting substances so that they remain loaded within the implant. Another purpose of the cap may be to add structural support to the implant. The cap may be solid or it may have openings therethrough. Any such openings could allow for the loaded material to stay within the implant while providing for vascular access to allow for the ingrowth of blood vessels and the growth of bone through the end of the implant.

For a posterior approach implant, the cap may be on either or both ends. The trailing end of the implant in a posterior approach implant has direct exposure to the spinal canal where the spinal cord and nerve roots are located. A cap on a posterior approach implant may be for the purpose of sealing off the spinal canal from the fusion-promoting substances contained in the hollow interior of the implant so that no bone grows into the canal. Further, the present invention implant may be used in combination with chemical substances and/or compounds applied at the trailing end of the implant to inhibit scar formation, and the cap may be of benefit in shielding the fusion-promoting substances contained in the implant from these scar formation inhibiting chemicals and compounds. It may also be for the purposes identified herein used in association with the leading end cap of an anterior approach implant.

Shown in FIGS. 14–16, in accordance with the present invention, as embodied and broadly described herein, is a second embodiment of an expandable threaded artificial interbody spinal fusion implant 200 for posterior insertion across a disc space D between two adjacent vertebral bodies V of a human spine. Threaded implant 200 of the present invention includes an upper member 202 having an arcuate portion 204 adapted for placement toward and at least in part within the upper of the adjacent vertebral bodies V and a lower member 206 having an arcuate portion 208 adapted for placement toward and at least in part within the lower of the adjacent vertebral bodies V.

Figure 14A:
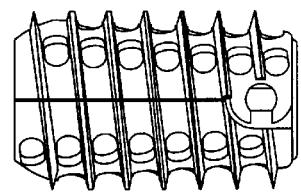
FIG. 14A is a side view of an alternative variation of a second embodiment of the implant of FIG. 14 for posterior insertion.

As shown in FIG. 14, implant 200 may be angled or tapered so as to converge from trailing end to leading end when in the collapsed position for insertion into the spine. The taper on implant 200 may facilitate its insertion. Alternatively, as shown in FIG. 14A, the implant of the present invention may be angled or tapered so as to diverge from trailing end to leading end when in the collapsed position for insertion into the spine. For an implant with an angle that diverges for trailing end to leading end, the leading end may have a chamfer or other configuration to reduce the size of the leading end to facilitate insertion of the implant into the spine.

Implant 200 in FIGS. 14 and 15 is shown being implanted into the spine from the posterior aspect with expander 222 on the distal end 226 or leading end 250 of implant 200. While anterior and posterior aspect approaches have been illustrated herein, the present invention is not limited to these illustrated approaches. In particular, but not limited thereto, the threaded implant of the present invention also may be used in threaded implants for insertion from the translateral aspect of the spine as disclosed by Michelson in U.S. Pat. No. 5,860,973, which is incorporated herein by reference.

As best shown in FIG. 16, tracks 232, 234 of upper and lower members 202, 206 of the second embodiment have a cooperating surface 266 and expander 222 has a corresponding cooperating surface 268 that contacts cooperating surface 266 of tracks 232, 234 to orient expander 222 in a predetermined location. The cooperating surfaces orient expander 222 within implant 200 such that the axis of rotation of expander 222 is parallel to the longitudinal axis of implant 200 and more particularly center expander 222 within implant 200 such that the axis of rotation of expander 222 coincides with longitudinal axis L of implant 200.

Tracks 232, 234 include sides 270 having cooperating surface 266 and expander 222 has corresponding cooperating surface 268 used to orient expander 122 in a predetermined location. Cooperating surface 266 of side 270 is a detent and corresponding cooperating surface 268 of expander 222 is a projection. The projection preferably projects away from expander 222 in a direction parallel to the longitudinal axis of implant 200. The detent and the projection preferably center expander 222 within implant 200 such that the axis of rotation of expander 222 coincides with the longitudinal axis of implant 200.

Figure 17:
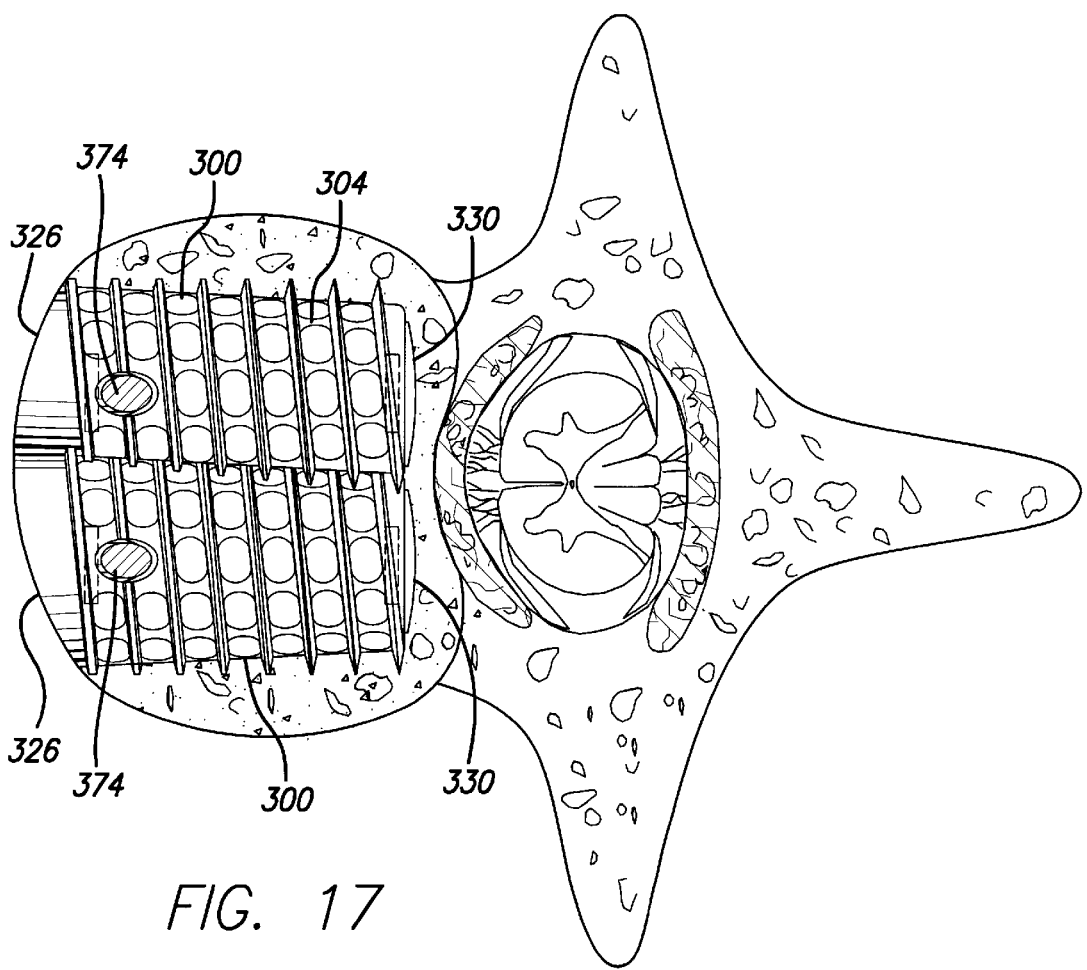
FIG. 17 is a top plan view of another embodiment of the present invention inserted upon the lower vertebral body of an implantation site formed anteriorly across a disc space with the vertebral body shown in partial cross-section.

Shown in FIGS. 17–19, in accordance with the present invention, as embodied and broadly described herein, is a third embodiment of an expandable threaded artificial interbody spinal fusion implant 300 for insertion across a disc space D between two adjacent vertebral bodies V of a human spine. Threaded implant 300 of the present invention includes an upper member 302 having an arcuate portion 304 for orientation toward the upper of adjacent vertebral bodies V and a lower member 306 having an arcuate portion 308 for orientation toward the lower of the adjacent vertebral bodies V.

Implant 300 of the present embodiment may include any of the various features disclosed in association with implant 100 and implant 200 disclosed herein. Implant 300 further includes a side surface 372 contoured to cooperatively receive another implant. See U.S. Pat. No. 5,593,409 by Michelson for a discussion of the advantages associated with placing implants in side-by-side contact.

Another aspect of implant 300 is that its upper and lower members 302, 306 have screw holes 374 passing therethrough adapted to receive a screw 378 passing from the interior of implant 300 into adjacent vertebral bodies V to anchor implant 300 to an adjacent vertebral body V.

Figure 20:
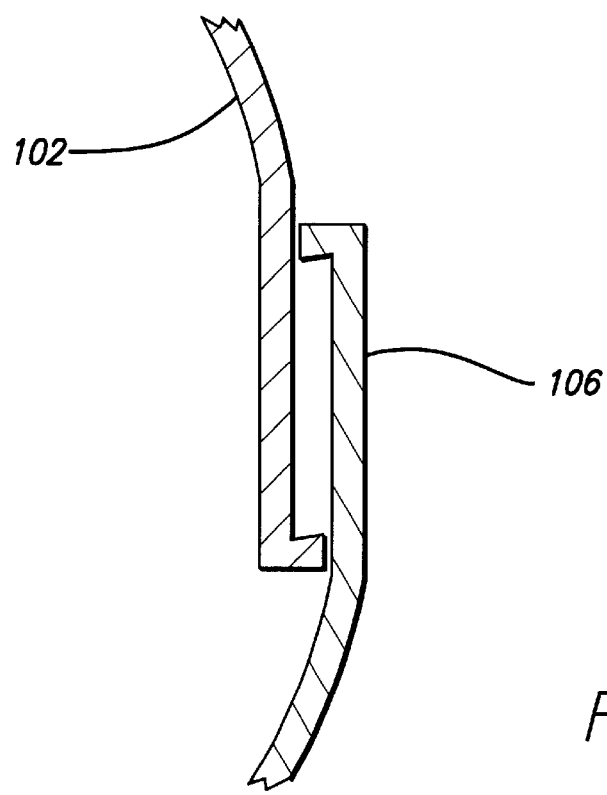
FIG. 20 is a partial cross sectional view of an embodiment of an interlocking wall design along line 21—21 of FIG. 19.
Figure 21:
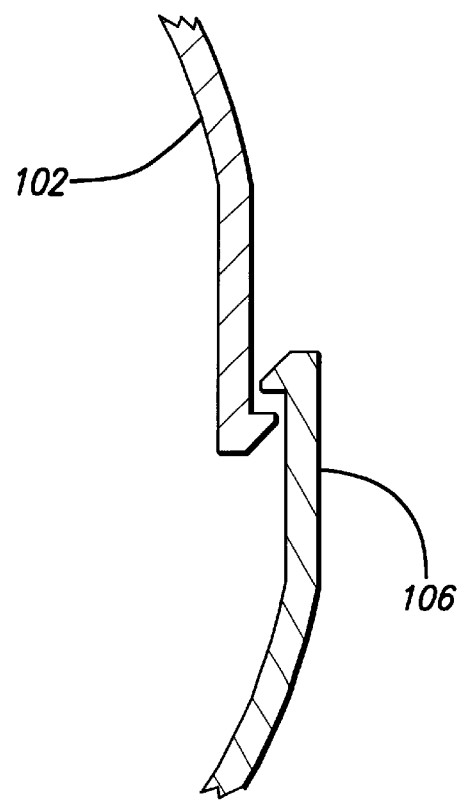
FIG. 21 is a partial cross sectional view of another embodiment of an interlocking wall design along line 21—21 of FIG. 19.

The articulation may be of one of two general types, examples of which are each herein disclosed. As shown in previously described embodiments of the present invention, the articulation may allow rotation about the articulation. A second type of articulation allows for both rotation and expansion at the point of articulation. An example of this is shown in FIG. 19, where a peg and hook design is utilized. While in this example both functions, that is rotation or pivoting, and captured or limited expansion with a fixed end point or stop, occur at the same location. Alternatively, and without departing from the teachings of the present invention, those functions can be divided. By way of example only, and not limitation, expansion can be allowed and controlled by an interlocking wall design, as shown by the interlocking members in the alternative embodiments of FIGS. 20 and 21. Various other structural features as would be obvious to one of ordinary skill in the art after the teachings herein can similarly be employed.

A fixed end point for the implant expansion is preferred for the proper functioning of the opposed bone screws. A purpose of the opposed bone screws is to rigidly secure the implant within the vertebral segment. A further purpose is to pull each of the adjacent vertebral bodies toward the implant and towards each other so as to have a construct resistant to the deleterious effects of vertebral rocking as may otherwise occur with spinal flexion and extension absent such restraint. If the articulation device captured the upper and lower members together, as in the embodiments of FIGS. 1–16, by closely encircling a post then the implant could not expand at that location. So the coupling mechanism of FIG. 19 permits the upper and lower members to remain articulated, permits the implant to expand, and permits the screws to pull against the implant and each other, in opposite directions and to pull the bones toward each other. The optional extended slot and peg configuration on the right-hand side of FIG. 19 illustrated in dashed image lines is not needed to hold the implant together.

In accordance with this embodiment of the present invention, a second expander may be located at least in part between the upper and lower members for moving at least a portion of the upper and lower members away from one another to increase the height of the implant defined by the maximum distance between the arcuate portions of the upper and lower members. All of the features described herein for the expander may also be applicable to the second expander. Additionally, the second expander may be located proximate an end of the implant opposite the other expander, thereby providing an implant capable of being expanded at both ends of implant. The increased height of the implant resulting from moving the two expanders may be the constant or varied along the length of the implant according to the desired configuration of the implant.

The expandable threaded spinal fusion implant may be made of artificial or naturally occurring materials suitable for implantation in the human spine. The implant can comprise bone including, but not limited to, cortical bone. The implant can also be formed of material other than bone, such as metal including, but not limited to, titanium and its alloys or ASTM material, surgical grade plastics, plastic composites, ceramics, or other materials suitable for use as a threaded spinal fusion implant. The plastics may be bioresorbable. The threaded spinal fusion implant of the present invention can further be formed of bone growth promoting materials, including but not limited to, bone morphogenetic proteins, hydroxyapatite, and genes coding for the production of bone. The threaded implant can be treated with a bone growth promoting substance, can be a source of osteogenesis, or can be at least in part bioabsorbable. The threaded implant of the present invention can be formed of a porous material.

The expandable threaded spinal fusion implant of the present invention may be coated with, comprised of, be used in combination with, or have a hollow for containing bone growth promoting materials, including but not limited to, bone morphogenetic proteins, hydroxyapatite, and genes coding for the production of bone. The threaded spinal fusion implant of the present invention can be formed of a material that intrinsically participates in the growth of bone from one of adjacent vertebral bodies V to the other of adjacent vertebral bodies V.

While various embodiments of the present invention are presented by way of example only and not limitation, common to each of them, is that the expandable threaded spinal fusion implant for insertion across disc space D between two adjacent vertebral bodies V of a human spine has an upper member having an arcuate portion adapted for placement toward and at least in part within the upper of the adjacent vertebral bodies V. The implant also has a lower member having an arcuate portion adapted for placement toward and at least in part within the lower of the adjacent vertebral bodies V. The arcuate portions of the upper and lower members have at least one opening. The openings of the upper and lower members are in communication with one another to permit for the growth of bone from vertebral body V to adjacent vertebral body V through the implant. At least a portion of a thread for engaging adjacent vertebral bodies V is on the exterior of each of the opposed arcuate portions of the upper and lower members. A blocker in the form of an expander preferably is located proximate at least one of the ends to hold at least a portion of the upper and lower members apart from one another to increase the implant height.

There is disclosed in the above description and the drawings implants, which fully and effectively accomplish the objectives of this invention. However, it will be apparent that variations and modifications of the disclosed embodiments may be made without departing from the principles of the invention or the scope of the appended claims.

What is claimed is:

1. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one blocker adapted to cooperatively engage and hold at least a portion of said upper and lower members apart so as to maintain the increased height of said implant and resist the collapse of said implant to the collapsed implant height when said implant is in a final deployed position, said blocker being located at a predetermined location along the length of said implant and remaining at the predetermined location in transitioning said implant from said first position to said second position.

2. The threaded implant of claim 1, further comprising a hollow defined between said upper and lower members in communication with said openings in each of said upper and lower members, said hollow being adapted to receive fusion-promoting substances.

3. The threaded implant of claim 2, further comprising a second hollow between said upper and lower members located between said blocker and said end of said implant proximate said blocker.

4. The threaded implant of claim 1, further in combination with a fusion promoting substance.

5. The threaded implant of claim 4, wherein said fusion promoting substance is bone morphogenetic protein.

6. The threaded implant of claim 4, wherein said fusion promoting substance includes hydroxyapatite.

7. The threaded implant of claim 4, wherein said fusion promoting substance is genes coding for the production of bone.

8. The threaded implant of claim 4, wherein said fusion promoting substance is bone.

9. The threaded implant of claim 2, wherein said hollow has a width that is unobstructed by any mechanism for moving said blocker.

10. The threaded implant of claim 9, wherein said implant has a constant width in both the collapsed height and the increased height.

11. The threaded implant of claim 9, wherein said blocker is located at least in part between said upper and lower members.

12. The threaded implant of claim 9, wherein said blocker is located proximate at least one of said ends of said upper and lower members.

13. The threaded implant of claim 9, wherein said blocker is adapted to cooperatively engage a tool used to move said blocker from an initial position to a final position to increase the height of said implant, said tool not being a part of said implant and being removed from said implant after moving said blocker into the final position.

14. The threaded implant of claim 9, wherein said implant has a width and said blocker has a width less than the width of said implant.

15. The threaded implant of claim 9, wherein each of said upper and lower members are adapted to cooperate with and to fixedly locate said blocker.

16. The threaded implant of claim 15, wherein each of said upper and lower members have a track configured to permit said blocker to seat therein.

17. The threaded implant of claim 16, wherein at least one of said tracks and said blocker are adapted to cooperate with each other to center said blocker along a longitudinal axis of said implant.

18. The threaded implant of claim 9, wherein said blocker moves said arcuate portions of said upper and lower members from a first angled orientation to a second angled orientation relative to one another.

19. The threaded implant of claim 9, wherein said blocker is an expander adapted to expand said implant from a first collapsed height to a second expanded height when moved from a first to a second position.

20. The threaded implant of claim 19, wherein said implant has a longitudinal axis and said expander rotates in a plane generally perpendicular to the longitudinal axis of said implant to increase the height of said implant.

21. The threaded implant of claim 19, wherein said expander is located along the length of said implant.

22. The threaded implant of claim 19, wherein said expander is located proximate said proximal ends of said upper and lower members.

23. The threaded implant of claim 19, wherein said hollow is substantially unobstructed by said expander extending along a substantial portion of the length of said hollow so as to permit growth of bone from adjacent vertebral body to adjacent vertebral body through said implant.

24. The threaded implant of claim 19, wherein said expander remains in the same location along the longitudinal axis of the implant when rotated.

25. The threaded implant of claim 19, wherein said expander is adapted to cooperatively engage a tool used to move said expander from an initial position to a final position to increase the height of said implant, said tool not being a part of said implant and being removed from said implant after moving said expander into the final position.

26. The threaded implant of claim 19, wherein said expander is adapted to cooperatively engage a tool that rotates about an axis parallel to the longitudinal axis of said implant to rotate said expander to increase the height of said implant.

27. The threaded implant of claim 26, wherein said expander rotates in a plane perpendicular to the longitudinal axis of siad implant to increase the height of said implant.

28. The threaded implant of claim 27, wherein said expander remains in the same location along the longitudinal axis of the implant when rotated.

29. The threaded implant of claim 19, wherein said expander moves said arcuate portions of said upper and lower members from an angled orientation to an angled orientation relative to one another.

30. The threaded implant of claim 19, wherein each of said upper and lower members are adapted to cooperate with said expander.

31. The threaded implant of claim 30, wherein said upper and lower members are adapted to cooperate with said expander so as to center said expander within a cross section of the upper and lower members.

32. The threaded implant of claim 30, wherein each of said upper and lower members have a track configured to permit said expander to rotate therein.

33. The threaded implant of claim 32, wherein said track of said upper member and said track of said lower member are in the same place.

34. The threaded implant of claim 32, wherein said track of said upper member and said track of said lower member are parallel to one another.

35. The threaded implant of claim 32, where said track of said upper member and said track of said lower member are in a plane perpendicular to the longitudinal axis of said implant.

36. The threaded implant of claim 32, wherein at least one of said tracks of said upper and lower members has a cooperating surface, said expander having a correspondence cooperating surface that contacts said cooperating surface of said at least one track to orient said expander in a predetermined location.

37. The threaded implant of claim 36, wherein said cooperating surfaces orient said expander within said implant such that the axis of rotation of said expander is parallel with the longitudinal axis of said implant.

38. The threaded implant of claim 37, wherein said cooperating surfaces center said expander within said implant such that the axis of rotation of said expander coincides with the longitudinal axis of said implant.

39. The threaded implant of claim 31, wherein at least one of said tracks of said upper and lower members includes at least one side having a cooperating surface, said expander having a corresponding cooperating surface that contacts said cooperating surface of said at least one side to orient said expander in a predetermined location.

40. The threaded implant of claim 39, wherein said cooperating surface of said at least one side is a detent and said corresponding cooperating surface of said expander is a projection.

41. The threaded implant of claim 40, wherein said detent and said projection center said expander within said implant such that the axis of rotation of said expander coincides with the longitudinal axis of said implant.

42. The threaded implant of claim 19, wherein said upper and lower members structurally cooperate with said expander so as to keep said expander located within said implant.

43. The threaded implant of claim 19, wherein said upper and lower members are configured to cooperate with one another so as to stop said upper and lower members from being moved apart from one another more than a predetermined distance.

44. The threaded implant of claim 19, wherein said expander has a first height corresponding to the height of said expander when said implant is initially inserted into the spine, said expander having a second height corresponding to the height of said expander when said expander is moved into a final deployed position to increase the height of said implant, said second height being greater than said first height.

45. The threaded implant of claim 44, wherein the difference between said first height and said second height of said expander approximates the difference in height of said implant between said first position and said second position as measured proximate the location of said expander.

46. The threaded implant of claim 19, wherein said expander has a depth dimension less than that of said first and second height of said expander.

47. The threaded implant of claim 46, wherein said expander has a fixed shape during movement from an initial insertion position to a final deployed position within said implant.

48. The threaded implant of claim 9, wherein said upper and lower members have walls contacting one another.

49. The threaded implant of claim 48, wherein said walls are aligned parallel with the longitudinal axis of said implant.

50. The threaded implant of claim 48, whereis said walls are at least in part overlapping.

51. The threaded implant of claim 9, wherein said upper and lower members have a rotational articulation therebetween adjacent one of said proximal end and said distal end of said upper and lower members.

52. The threaded implant of claim 51, wherein said rotational articulation is at one of said proximal end and said distal end of said upper and lower members opposite said blocker.

53. The threaded implant of claim 51, wherein said rotational articulation allows for expansion.

54. The threaded implant of claim 53, wherein said rotational articulation allows for limited expansion.

55. The threaded implant of claim 9, wherein one of said upper and lower members has an interior wall, which is exposed, extending therefrom toward the other of said upper and lower members when said implant is in an initial insertion position, and when said implant is in a final position said implant has a shape such that each of said arcuate portions of said upper and lower members are separated by at least a portion of said interior wall, which now has an exposed side.

56. The threaded implant of claim 55, wherein said upper and lower members have side walls for engaging each other.

57. The threaded implant of claim 56, wherein said side walls of said upper and lower members are at least partially overlapping walls.

58. The threaded implant of claim 55, wherein said arcuate portions of said upper and lower members form an angular orientation relative to one another when said implant is in the final position.

59. The threaded implant of claim 55, wherein said arcuate portions of said upper and lower members when said implant is in the initial insertion position form a frusto-conical shape.

60. The threaded implant of claim 9, further comprising a cap for closing one of said proximal end and said distal end of said upper and lower members, said cap having an exterior surface and an interior surface.

61. The threaded implant of claim 60, wherein said interior surface of said cap has spaced slots about its circumference to facilitate a snap fit of said cap into said implant.

62. The threaded implant of claim 9, wherein said implant comprises an artificial material other than bone.

63. The threaded implant of claim 9, wherein said implant is made of an artificial material that is stronger than bone.

64. The threaded implant of claim 9, wherein said implant is made of an artificial material that is harder than bone.

65. The threaded implant of claim 9, wherein said implant comprises bone.

66. The threaded implant of claim 65, wherein said bone includes cortical bone.

67. The threaded implant of claim 9, wherein said implant comprises bone growth promoting material.

68. The threaded implant of claim 67, wherein said bone growth promoting material is bone morphogenetic protein.

69. The threaded implant of claim 67, wherein said bone growth promoting material is hydroxyapatite.

70. The threaded implant of claim 67, wherein said bone growth promoting material is genes coding for the production of bone.

71. The threaded implant of claim 9, wherein said implant is treated with a bone growth promoting substance.

72. The threaded implant of claim 9, wherein said implant is a source of osteogenesis.

73. The threaded implant of claim 9, wherein said implant is at least in part bioabsorbable.

74. The threaded implant of claim 9, wherein said implant comprises metal.

75. The threaded implant of claim 74, wherein said metal is ASTM material suitable for use said threaded spinal fusion implant.

76. The threaded implant of claim 74, wherein said metal includes titanium.

77. The threaded implant of claim 9, wherein said implant comprises a plastic material.

78. The threaded implant of claim 9, wherein said implant comprises a ceramic material.

79. The threaded implant of claim 9, wherein said implant is formed of a porous material.

80. The threaded implant of claim 9, wherein said implant is formed of a material that intrinsically participates in the growth of bone from adjacent vertebral body to adjacent vertebral body through said implant.

81. The threaded implant of claim 9, wherein said implant has an interior surface and a hollow defined therein, said hollow being capable of containing bone growth promoting material.

82. The threaded implant of claim 81, wherein said bone growth promoting material is bone morphogenetic protein.

83. The threaded implant of claim 81, wherein said bone growth promoting material is hydroxyapatite.

84. The threaded implant of claim 81, wherein said bone growth promoting material is genes coding for the production of bone.

85. The threaded implant of claim 9, wherein said at least one opening is adapted to retain fusion-promoting materials.

86. The threaded implant of claim 9, wherein at least a portion of said implant is treated to promote bone ingrowth between said implant and said adjacent vertebral bodies.

87. The threaded implant of claim 9, in combination with a chemical substance to inhibit scar formation.

88. The threaded implant of claim 17, wherein said expander is located proximate said distal ends of said upper and lower members.

89. The threaded implant of claim 9, wherein said implant has a side surface when in a final position that is contoured to cooperate with another implant.

90. The threaded implant of claim 89, wherein said implant and said cooperating other implant have a combined width therebetween less than the combined height of said implant and said cooperating other implant.

91. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one blocker adapted to cooperatively engage and hold at least a portion of said upper and lower members apart so as to maintain the increased height of said implant and resist the collapse of said implant to the collapsed implant height when said implant is in a final deployed position, said implant having side walls and said blocker not contacting said side walls when said implant is in the final deployed position.

92. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to cooperatively engage and hold at least a portion of said upper and lower members apart so as to maintain the increased height of said implant and resist the collapse of said implant to the collapsed implant height when said implant is in a final deployed position, said expander being adapted to expand said implant from a first collapsed height to a second expanded height when moved from a first to a second position, each of said upper and lower members being adapted to cooperate with said expander, each of said upper and lower members having a track configured to permit said expander to rotate therein, said tracks permitting said expander to move from side to side within said track.

93. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to cooperatively engage and hold at least a portion of said upper and lower members apart so as to maintain the increased height of said implant and resist the collapse of said implant to the collapsed implant height when said implant is in a final deployed position, said expander being adapted to expand said implant from a first collapsed height to a second expanded height when moved from a first to a second position, said expander having an upper surface, a lower surface, and side surfaces as defined when said expander is positioned to increase the height of said implant, said side surfaces intersecting said upper and said lower surfaces at two diametrically opposed junctions.

94. The threaded implant of claim 93, wherein said two diametrically opposed junctions are a pair of diametrically opposed corners and a pair of diametrically opposed arcs.

95. The threaded implant of claim 94, wherein said two diametrically opposed arcs are each of the same radius.

96. The threaded implant of claim 95, wherein the distance across said two diametrically opposed arcs generally approximates the distance between said upper and lower surfaces of said expander.

97. The threaded implant of claim 94, wherein said two diametrically opposed corners form a 90-degree angle.

98. The threaded implant of claim 93, wherein each of said upper and lower surfaces lie generally in a plane.

99. The threaded implant of claim 93, wherein said upper and lower surfaces are generally parallel to one another.

100. The threaded implant of claim 93, wherein said side surfaces and said upper and lower surfaces are oriented to substantially form a parallelogram.

101. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members having a rotational articulation therebetween adjacent one of said proximal ends and said distal ends of said upper and lower members and allowing for expansion of the height of said implant, said rotational articulation being formed by said upper and lower members interdigitating so as to cooperatively engage said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one blocker adapted to cooperatively engage and hold at least a portion of said upper and lower members apart so as to maintain the increased height of said implant and resist the collapse of said implant to the collapsed implant height when said implant is in a final deployed position.

102. The threaded implant of claim 101, wherein said rotational articulation is configured such that engagement occurs when said upper and lower members are substantially perpendicular to one another.

103. The threaded implant of claim 102, wherein said rotational articulation is configured to remain engaged within a range of movement of said upper and lower members resulting from positioning said implant in the second position.

104. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander said first height and said second height being in a plane, the plane being perpendicular to the axis of rotation of said expander inserted.

105. The threaded implant of claim 104, further comprising a hollow defined between said upper and lower members in communication with said openings in each of said upper and lower members, said hollow being adapted to receive fusion-promoting substances, said hollow having a width that is substantially unobstructed by any mechanism for moving said expander.

106. The threaded implant of claim 104, wherein said implant has a constant width in both the collapsed height and the increased height.

107. The threaded implant of claim 104, wherein said implant has a width and said expander has a width less than the width of said implant.

108. The threaded implant of claim 104, wherein said implant has a width and said expander has a width less than one half the width of said implant.

109. The threaded implant of claim 104, wherein said implant has a longitudinal axis and said expander rotates in a plane generally perpendicular to the longitudinal axis of said implant to increase the height of said implant.

110. The threaded implant of claim 104, wherein said expander is located along the length of said implant.

111. The threaded implant of claim 104, wherein said expander is located proximate said proximal ends of said upper and lower members.

112. The threaded implant of claim 104, wherein said expander is adapted to cooperatively engage a tool used to move said expander from an initial position to a final position to increase the height of said implant, said tool not being a part of said implant and being removed from said implant after moving said expander into the final position.

113. The threaded implant of claim 104, wherein said expander is adapted to cooperatively engage a tool that rotates about an axis parallel to the longitudinal axis of said implant to rotate said expander to increase the height of said implant.

114. The threaded implant of claim 113, wherein said expander rotates in a plane perpendicular to the longitudinal axis of said implant to increase the height of said implant.

115. The threaded implant of claim 114, wherein said expander remains in the same location along the longitudinal axis of the implant when rotated.

116. The threaded implant of claim 104, wherein said expander moves said arcuate portions of said upper and lower members from a first angled orientation to a second angled orientation relative to one another.

117. The threaded implant of claim 104, wherein each of said upper and lower members are adapted to cooperate with said expander.

118. The threaded implant of claim 117, wherein said upper and lower members are adapted to cooperate with said expander so as to center said expander within a cross section of the upper and lower members.

119. The threaded implant of claim 117, wherein each of said upper and lower members have a track configured to permit said expander to rotate therein.

120. The threaded implant of claim 119, wherein said track of said upper member and said track of said lower member are in the same plane.

121. The threaded implant of claim 119, wherein said track of said upper member and said track of said lower member are parallel to one another.

122. The threaded implant of claim 119, where said track of said upper member and said track of said lower member are in a plane perpendicular to the longitudinal axis of said implant.

123. The threaded implant of claim 118, wherein at least one of said tracks of said upper and lower members has a cooperating surface, said expander having a corresponding cooperating surface that contacts said cooperating surface of said at least one track to orient said expander in a predetermined location.

124. The threaded implant of claim 123, wherein said cooperating surfaces orient said expander within said implant such that the axis of rotation of said expander is parallel with the longitudinal axis of said implant.

125. The threaded implant of claim 124, wherein said cooperating surfaces center said expander within said implant such that the axis of rotation of said expander coincides with the longitudinal axis of said implant.

126. The threaded implant of claim 118, wherein at least one of said tracks of said upper and lower members includes at least one side having a cooperating surface, said expander having a corresponding cooperating surface that contacts said cooperating surface of said at least one side to orient said expander in a predetermined location.

127. The threaded implant of claim 126, wherein said cooperating surface of said at least one side is a detent and said corresponding cooperating surface of said expander is a projection.

128. The threaded implant of claim 127, wherein said detent and said projection center said expander within said implant such that the axis of rotation of said expander coincides with the longitudinal axis of said implant.

129. The threaded implant of claim 104, wherein said upper and lower members structurally cooperate with said expander so as to keep said expander located within said implant.

130. The threaded implant of claim 104, wherein said upper and lower members are configured to cooperate with one another so as to stop said upper and lower members from being moved apart from one another more than a predetermined distance.

131. The threaded implant of claim 104, wherein the difference between said first height and said second height of said expander approximates the difference in height of said 131. implant between said first position and said second position as measured proximate the location of said expander.

132. The threaded implant of claim 104, wherein said expander has a depth dimension less than that of said first and second height of said expander.

133. The threaded implant of claim 132, wherein said expander has a fixed shape during movement from an initial insertion position to a final deployed position within said implant.

134. The threaded implant of claim 104, wherein said upper and lower members have walls contacting one another.

135. The threaded implant of claim 135, wherein said walls are aligned parallel with the longitudinal axis of said implant.

136. The threaded implant of claim 134, wherein said walls are at least in part overlapping.

137. The threaded implant of claim 104, wherein said upper and lower members have a rotational articulation therebetween adjacent one of said proximal end and said distal end of said upper and lower members.

138. The threaded implant of claim 137, wherein said rotational articulation is at one of said proximal end and said distal end of said upper and lower members opposite said expander.

139. The threaded implant of claim 137, wherein said rotational articulation allows for expansion.

140. The threaded implant of claim 139, wherein said rotational articulation allows for limited expansion.

141. The threaded implant of claim 104, wherein one of said upper and lower members has an interior wall, which is unexposed, extending therefrom toward the other of said upper and lower members when said implant is in an initial insertion position, and when said implant is in a final position said implant has a shape such that each of said arcuate portions of said upper and lower members are separated by at least a portion of said interior wall, which now has an exposed side.

142. The threaded implant of claim 141, wherein said upper and lower members have side walls for engaging each other.

143. The threaded implant of claim 142, wherein said side walls of said upper and lower members are at least partially overlapping walls.

144. The threaded implant of claim 141, wherein said arcuate portions of said upper and lower members form an angular orientation relative to one another when said implant is in the final position.

145. The threaded implant of claim 141, wherein said arcuate portions of said upper and lower members when said implant is in the initial insertion position form a frusto-conical shape.

146. The threaded implant of claim 104, further comprising a cap for closing one of said proximal end and said distal end of said upper and lower members, said cap having an exterior surface and an interior surface.

147. The threaded implant of claim 146, wherein said interior surface of said cap has spaced slots about its circumference to facilitate a snap fit of said cap into said implant.

148. The threaded implant of claim 104, wherein said implant comprises an artificial material other than bone.

149. The threaded implant of claim 104, wherein said implant is made of an artificial material that is stronger than bone.

150. The threaded implant of claim 104, wherein said implant is made of an artificial material that is harder than bone.

151. The threaded implant of claim 104, wherein said implant comprises bone.

152. The threaded implant of claim 151, wherein said bone includes cortical bone.

153. The threaded implant of claim 104, wherein said implant comprises bone growth promoting material.

154. The threaded implant of claim 153, wherein said bone growth promoting material is bone morphogenetic protein.

155. The threaded implant of claim 153, wherein said bone growth promoting material is hydroxyapatite.

156. The threaded implant of claim 155, wherein said bone growth promoting material is genes coding for the production of bone.

157. The threaded implant of claim 104, wherein said implant is treated with a bone growth promoting substance.

158. The threaded implant of claim 104, wherein said implant is a source of osteogenesis.

159. The threaded implant of claim 104, wherein said implant is at least in part bioabsorbable.

160. The threaded implant of claim 104, wherein said implant comprises metal.

161. The threaded implant of claim 160, wherein said metal is ASTM material suitable for use said threaded spinal fusion implant.

162. The threaded implant of claim 160, wherein said metal includes titanium.

163. The threaded implant of claim 104, wherein said implant comprises a plastic material.

164. The threaded implant of claim 104, wherein said implant comprises a ceramic material.

165. The threaded implant of claim 104, wherein said implant is formed of a porous material.

166. The threaded implant of claim 104, wherein said implant is formed of a material that intrinsically participates in the growth of bone from adjacent vertebral body to adjacent vertebral body through said implant.

167. The threaded implant of claim 104, wherein said implant has an interior surface and a hollow defined therein, said hollow being capable of containing bone growth promoting material.

168. The threaded implant of claim 167, wherein said bone growth promoting material is bone morphogenetic protein.

169. The threaded implant of claim 167, wherein said bone growth promoting material is hydroxyapatite.

170. The threaded implant of claim 167, wherein said bone growth promoting material is genes coding for the production of bone.

171. The threaded implant of claim 104, wherein said at least one opening is adapted to retain fusion-promoting materials.

172. The threaded implant of claim 104, wherein at least a portion of said implant is treated to promote bone ingrowth between said implant and said adjacent vertebral bodies.

173. The threaded implant of claim 104, in combination with a chemical substance to inhibit scar formation.

174. The threaded implant of claim 104, wherein said expander is located proximate said distal ends of said upper and lower members.

175. The threaded implant of claim 104, wherein said implant has a side surface when in a final position that is contoured to cooperate with another implant.

176. The threaded implant of claim 175, wherein said implant and said cooperating other implant have a combined width therebetween less than the combined height of said implant and said cooperating other implant.

177. The threaded implant of claim 104, further in combination with a fusion promoting substance.

178. The threaded implant of claim 177, wherein said fusion promoting substance is bone morphogenetic protein.

179. The threaded implant of claim 177, wherein said fusion promoting substance includes hydroxyapatite.

180. The threaded implant of claim 177, wherein said fusion promoting substance is genes coding for the production of bone.

181. The threaded implant of claim 177, wherein said fusion promoting substance is bone.

182. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander, said implant having side walls and said expander not contacting said side walls when said implant is in the final deployed position.

183. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander, said expander remaining in the same location along the longitudinal axis of the implant when rotated.

184. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander, said expander being located at a predetermined location along the length of said implant and remaining so located in transitioning said implant from the first position to the second position.

185. A threaded interbody spinal fusion implant for at least in part rotational insertion across a disc space between two adjacent vertebral bodies of a spine, said implant comprising:

an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;

a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;

at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander, each of said upper and lower members being adapted to cooperate with said expander, each of said upper and lower members having a track configured to permit said expander to rotate therein, said tracks permitting said expander to move from side to side within said track.

186. A threaded interbody spinal fusion implant for at least in part rotational insertion across a disc space between two adjacent vertebral bodies of a spine, said implant comprising:
   an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;
   a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating therebetween adjacent one of said proximal ends and said distal ends of said upper and lower members and allowing for expansion of the height of said implant, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;
   at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and
   at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander, said expander having an upper surface, a lower surface, and side surfaces as defined when said expander is positioned to increase the height of said implant, said side surfaces intersecting said upper and said lower surfaces at two diametrically opposed junctions.

187. The threaded implant of claim 186, wherein said two diametrically opposed junctions are a pair of diametrically opposed corners and a pair of diametrically opposed arcs.

188. The threaded implant of claim 186, wherein each of said upper and lower surfaces lie generally in a plane.

189. The threaded implant of claim 186, wherein said upper and lower surfaces are generally parallel to one another.

190. The threaded implant of claim 186, wherein said side surfaces and said upper and lower surfaces are oriented to substantially form a parallelogram.

191. The threaded implant of claim 187, wherein said two diametrically opposed arcs are each of the same radius.

192. The threaded implant of claim 191, wherein the distance across said two diametrically opposed arcs generally approximates the distance between said upper and lower surfaces of said expander.

193. The threaded implant of claim 187, wherein said two diametrically opposed corners form a 90-degree angle.

194. A threaded interbody spinal fusion implant for at least in part rotational insertion across a disc space between two adjacent vertebral bodies of a spine, said implant comprising:
   an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;
   a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members having a rotational articulation therebetween adjacent one of said proximal ends and said distal ends of said upper and lower members and allowing for expansion of the height of said implant, said rotational articulation being formed by said upper and lower members interdigitating so as to cooperatively engage, said upper and lower members having a first position relative to one another allowing for a collapsed implant height and a second position relative to one another allowing for an increased height, said arcuate portions of said upper and lower members in the first position being angled to one another over a substantial portion of the length of said implant and forming at least a portion of a frusto-conical shape along the length of said implant;
   at least a portion of a helical thread formed on the exterior of each of said opposed arcuate portions of said upper and lower members for penetrably engaging the adjacent vertebral bodies and to facilitate securing said implant into the spine by at least in part rotating said implant about the longitudinal axis of said implant; and
   at least one expander adapted to expand said upper and lower members from the first position to the second position when moved from an expander insertion position to a final deployed expander position, said expander being adapted to cooperatively engage and hold at least a portion of said upper and lower members apart so as to maintain the increased height of said implant and resist the collapse of said implant to the collapsed implant height when said implant is in a final deployed position, said expander having a first height corresponding to the height of said expander when said implant is initially inserted into the spine, said expander having a second height corresponding to the height of said expander when said expander is rotated into a final deployed position to increase the height of said implant, said second height of said expander being greater than said first height of said expander.

195. The threaded implant of claim 194, wherein said rotational articulation is configured such that engagement occurs when said upper and lower members are substantially perpendicular to one another.

196. The threaded implant of claim 195, wherein said rotational articulation is configured to remain engaged within a range of movement of said upper and lower members resulting from positioning said implant in the second position.

197. The threaded implant of claim 9, further comprising a second blocker located between said upper and lower members for holding at least a portion of the upper and lower members apart where said second expander is located.

198. The threaded implant of claim 19 further comprising a second expander located between said upper and lower members for moving at least a portion of the upper and lower members away from one another to increase the maximum height of said implant where said second expander is located.

199. The threaded implant of claim 198, wherein said second expander rotates to increase the height of said implant.

200. The threaded implant of claim 198, wherein said second expander is located proximate an end of said imnplant opposite said expander.

201. The threaded implant of claim 198, wherein said implant has a longitudinal axis and said second expander rotates in a plane perpendicular to the longitudinal axis of said implant to increase the height of said implant.

202. The threaded implant of claim 200, wherein said hollow is substantially unobstructed by said second expander extending along a substantial portion of the length of said hollow so as to permit growth of bone from adjacent vertebral body to adjacent vertebral body through said implant.

203. The threaded implant of claim 200, wherein said second expander remains in the same location along the longitudinal axis of the implant when rotated.

204. The threaded implant of claim 198, wherein said second expander is located proximate one of the proximal end and the distal end of said upper and lower members.

205. The threaded implant of claim 204, wherein said hollow is unobstructed by said second expander extending along a substantial portion of the length of said hollow to permit growth of bone from adjacent vertebral body to adjacent vertebral body through said implant.

206. The threaded implant of claim 204, further comprising a second hollow between said upper and lower member located between said second expander and said end of said implant proximate said second expander.

207. The threaded implant of claim 198, wherein each of said upper and lower members have a track within which said second expander rotates.

208. The threaded implant of claim 198, wherein said track is configured to permit said second expander to rotate therein and then to move from side to side within said track.

209. The threaded implant of claim 198, wherein said second expander has a first height corresponding to the height of said second expander when said implant is initially inserted into the spine, said second expander having a second height corresponding to the height of said second expander when said second expander is moved into a final deployed position to increase the height of said implant, said second height being greater than said first height.

210. The threaded implant of claim 198, wherein said second expander has an upper surface, a lower surface, and side surfaces as defined when said second expander is positioned to increase the height of said implant, and said side surfaces intersecting said upper and said lower surfaces at two diametrically opposed junctions.

211. The threaded implant of claim 210, wherein the difference between said first height and said second height of said second expander approximates the difference in height of said implant between said first position and said second position as measured proximate the location of said second expander.

212. The threaded implant of claim 9, wherein said implant has an interior, at least one of said upper and lower members has a screw hole passing therethrough adapted to receive a screw passing from said interior of said implant into one of the adjacent vertebral bodies.

213. The threaded implant of claim 212, wherein each of said upper and lower members has at least one screw hole passing therethrough adapted to receive a screw passing from said interior of said implant into the adjacent vertebral body in contact with each of said upper and lower members respectively.

214. The threaded implant of claim 212, further comprising at least one screw adapted to pass from said interior of said implant through said screw hole and into the adjacent vertebral body to anchor said implant to the adjacent vertebral body.

215. The threaded implant of claim 9, wherein said blocker is an expander having an external thread, each of said upper and lower members having a threaded converging portion adapted to cooperate with said external thread of said expander to expand said implant from a first collapsed height to a second expanded height when said expander is rotated from a first to a second position.

216. The threaded implant of claim 104, further comprising a second expander located between said upper and lower members for moving at least a portion of the upper and lower members away from one another to increase the maximum height of said implant where said second expander is located.

217. The threaded implant of claim 216, wherein said second expander rotates to increase the height of said implant.

218. The threaded implant of claim 216, wherein said second expander is located proximate an end of said implant opposite said expander.

219. The threaded implant of claim 216, wherein said implant has a longitudinal axis and said second expander rotates in a plane perpendicular to the longitudinal axis of said implant to increase the height of said implant.

220. The threaded implant of claim 218, wherein said hollow is substantially unobstructed by said second expander extending along a substantial portion of the length of said hollow so as to permit growth of bone from adjacent vertebral body to adjacent vertebral body through said implant.

221. The threaded implant of claim 218, wherein said second expander remains in the same location along the longitudinal axis of the implant when rotated.

222. The threaded implant of claim 216, wherein said second expander is located proximate one of the proximal end and the distal end of said upper and lower members.

223. The threaded implant of claim 222, wherein said hollow is unobstructed by said second expander extending along a substantial portion of the length of said hollow to permit growth of bone from adjacent vertebral body to adjacent vertebral body through said implant.

224. The threaded implant of claim 222, further comprising a second hollow between said upper and lower member located between said second expander and said end of said implant proximate said second expander.

225. The threaded implant of claim 216, wherein each of said upper and lower members have a track within which said second expander rotates.

226. The threaded implant of claim 225, wherein said track is configured to permit said second expander to rotate therein and then to move from side to side within said track.

227. The threaded implant of claim 216, wherein said second expander has a first height corresponding to the height of said second expander when said implant is initially inserted into the spine, said second expander having a second height corresponding to the height of said second expander when said second expander is moved into a final deployed position to increase the height of said implant, said second height being greater than said first height.

228. The threaded implant of claim 216, wherein said second expander has an upper surface, a lower surface, and side surfaces as defined when said second expander is positioned to increase the height of said implant, and said side surfaces intersecting said upper and said lower surfaces at two diametrically opposed junctions.

229. The threaded implant of claim 228, wherein the difference between said first height and said second height of said second expander approximates the difference in height of said implant between said first position and said second position as measured proximate the location of said second expander.

230. The threaded implant of claim 104, wherein said implant has an interior, at least one of said upper and lower members has a screw hole passing therethrough adapted to receive a screw passing from said interior of said implant into one of the adjacent vertebral bodies.

231. The threaded implant of claim 230, wherein each of said upper and lower members has at least one screw hole passing therethrough adapted to receive a screw passing from said interior of said implant into the adjacent vertebral body in contact with each of said upper and lower members respectively.

232. The threaded implant of claim 230, further comprising at least one screw adapted to pass from said interior of said implant through said screw hole and into the adjacent vertebral body to anchor said implant to the adjacent vertebral body.

233. The threaded implant of claim 104, wherein said blocker is an expander having an external thread, each of said upper and lower members having a threaded converging portion adapted to cooperate with said external thread of said expander to expand said implant from a first collapsed height to a second expanded height when said expander is rotated from a first to a second position.

* * * * *

UNITED STATES PATENT AND TRADEMARK OFFICE
CERTIFICATE OF CORRECTION

PATENT NO.    : 6,814,756 B1
DATED         : November 9, 2004
INVENTOR(S)   : Gary K. Michelson It is certified that error appears in the above-identified patent and that said Letters Patent is hereby corrected as shown below:

Column 22,
Line 3, change "place" to -- plane --;
Line 7, change "where" to -- wherein --;
Line 13, change "correspondence" to -- corresponding --;
Line 25, change "claim 31" to -- claim 32 --; and
Line 43, change "claim 19" to -- claim 9 --.

Column 23,
Line 6, change "whereis" to -- wherein --; and
Line 22, change "exposed" to -- unexposed --.

Column 24,
Line 42, change "claim 17" to -- claim 19 --.

Column 29,
Line 28, delete "inserted".

Column 30,
Line 24, change "where" to -- wherein --; and
Lines 28 and 42, change "claim 118" to -- claim 119 --.

Column 31,
Line 13, change "claim 135" to -- claim 134 --.

Column 32,
Line 12, change "claim 155" to -- claim 153 --.

Column 33,
Line 3, change "whereIn" to -- wherein --.

UNITED STATES PATENT AND TRADEMARK OFFICE
CERTIFICATE OF CORRECTION

PATENT NO.   : 6,814,756 B1
DATED        : November 9, 2004
INVENTOR(S)  : Gary K. Michelson It is certified that error appears in the above-identified patent and that said Letters Patent is hereby corrected as shown below:

Column 39,
Line 37, change "said imn-" to -- said im- --.

Signed and Sealed this

Twenty-second Day of March, 2005

JON W. DUDAS
*Director of the United States Patent and Trademark Office*